United States Patent
Wintermark

(10) Patent No.: US 10,537,575 B2
(45) Date of Patent: Jan. 21, 2020

(54) PHOSPHODIESTERASE INHIBITORS TO REPAIR BRAIN AND/OR RETINAL INJURY IN HUMAN NEWBORNS

(71) Applicant: Pia Wintermark, Montréal (CA)

(72) Inventor: Pia Wintermark, Montréal (CA)

( * ) Notice: Subject to any disclaimer, the term of this patent is extended or adjusted under 35 U.S.C. 154(b) by 0 days.

(21) Appl. No.: 15/663,915

(22) Filed: Jul. 31, 2017

(65) Prior Publication Data

US 2018/0042927 A1  Feb. 15, 2018

Related U.S. Application Data

(60) Provisional application No. 62/372,860, filed on Aug. 10, 2016.

(51) Int. Cl.
*A61K 31/513* (2006.01)
*A61K 9/00* (2006.01)

(52) U.S. Cl.
CPC .......... *A61K 31/513* (2013.01); *A61K 9/0053* (2013.01)

(58) Field of Classification Search
CPC .................................................... A61K 31/513
USPC .................................................... 514/252.06
See application file for complete search history.

(56) References Cited

PUBLICATIONS

Charriaut-Marlangue, Sildenafil Mediates Blood-Flow Redistribution and Neuroprotection After Neonatal Hypoxia-Ischemia, 2014, Stroke, vol. 45, pp. 850-856. (Year: 2014).*
Ashman et al. Sildenafil exposure in neonates with pulmonary hypertension after administration via a nasogastric tube, 2009, Arch Dis Child Fetal Neonatal Ed, vol. 95, pp. F109-F114. (Year: 2009).*
Baquero et al. Oral sildenafil in infants with persistent pulmonary hypertension of the newborn: a pilot randomized blinded study, 2006, Pediatrics, vol. 117, No. 4, pp. 1077-1083. (Year: 2006).*
Recker R, Adami A, Tone B, Tian HR, Lalas S, Hartman RE, Obenaus A, Ashwal S: Rodent neonatal bilateral carotid artery occlusion with hypoxia mimics human hypoxic-ischemic injury. J Cereb Blood Flow Metab 2009; 29: 1305-1316.
Hamers FPT, Koopmans GC, Joosten E: CatWalk-assisted gait analysis in the assessment of spinal cord injury. J Neurotrauma 2006; 23: 537-548.
Hetze S, Romer C, Teufelhart C, Meisel A, Engel O: Gait analysis as a method for assessing neurological outcome in a mouse model of stroke. J Neurosci Methods 2012; 206: 7-14.
Lubjuhn J, Gastens A, von Wilpert G, Bargiotas P, Herrmann O, Murikinati S, Rabie T, Marti HH, Amende I, Hampton TG, Schwaninger M: Functional testing in a mouse stroke model induced by occlusion of the distal middle cerebral artery. J Neurosci Methods 2009; 184: 95-103.
Parkkinen S, Ortega FJ, Kuptsova K, Huttunen J, Tarkka I, Jolkkonen J: Gait impairment in a rat model of focal cerebral ischemia. Stroke Res Treat 2013; 2013: 410972.
Wang Y, Bontempi B, Hong SM, Mehta K, Weinstein PR, Abrams GM, Liu J: A comprehensive analysis of gait impairment after experimental stroke and the therapeutic effect of environmental enrichment in rats. J Cereb Blood Flow Metab 2008; 28: 1936-1950.
Rasband WS: ImageJ. Bethesda, MD: U.S. National Institutes of Health, 1997-2004. Available at: http://imagej.nih.gov/ij.
Hendrickson ML, Rao AJ, Demerdash ON, Kalil RE: Expression of nestin by neural cells in the adult rat and human brain. PLoS One 2011; 6: e18535.
Springer ML: Assessment of myocardial angiogenesis and vascularity in small animal models. Methods Mol Biol 2010; 660: 149-167.
Ndode-Ekane XE, Hayward N, Gröhn O, Pitkänen A: Vascular changes in epilepsy: functional consequences and association with network plasticity in pilocarpine-induced experimental epilepsy. Neuroscience 2010; 166: 312-332.
Hallene KL, Oby E, Lee BJ, Santaguida S, Bassanini S, Cipolla M, Marchi N, Hossain M, Battaglia G, Janigro D: Prenatal exposure to thalidomide, altered vasculogenesis, and CNS malformations. Neuroscience 2006; 142: 267-283.
Iwai M, Cao G, Yin W, Stetler RA, Liu J, Chen J: Erythropoietin promotes neuronal replacement through revascularization and neurogenesis after neonatal hypoxia/ischemia in rats. Stroke 2007; 38: 2795-2803.
Noguchi T, Yoshiura T, Hiwatashi A, Togao O, Yamashita K, Nagao E, Shona T, Mizoguchi M, Nagata S, Sasaki T, Suzuki SO, Iwaki T, Kobayashi K, Mihara F, Honda H: Perfusion imaging of brain tumors using arterial spin-labeling: Correlation with histopathologic vascular density. Am J Neuroradiol 2008; 29: 688-693.
Rigau V, Morin M, Rousset MC, de Bock F, Lebrun A, Coubes P, Picot MC, Baldy-Moulinier M, Bockaert J, Crespel A, Lerner-Natoli M: Angiogenesis is associated with blood-brain barrier permeability in temporal lobe epilepsy. Brain 2007; 130: 1942-1956.
Wintermark P, Lechpammer M, Warfield SK, Kosaras B, Takeoka M, Poduri A, Madsen JR, Bergin AM, Whalen S, Jensen FE: Perfusion imaging of focal cortical dysplasia using arterial spin labeling: Correlation with histopathological vascular density. J Child Neural 2013; 28: 1474-1482.
Tong XK, Nicolakakis N, Kocharyan A, Hamel E: Vascular remodeling versus amyloid beta-induced oxidative stress in the cerebrovascular dysfunctions associated with Alzheimer's disease. J Neurosci 2005; 25: 11165-11174. Foresta C, Caretta N, Zuccarello D, et al. Expression of the PDE5 enzyme on human retinal tissue: new aspects of PDE5 inhibitors ocular side effects. Eye (Lond). 2008;22:144-149.
Hood DC, Birch DG. The A-wave of the human electroretinogram and rod receptor function. Invest Ophthalmol Vis Sci. 1990;31:2070-2081.
Miller RF, Dowling JE. Intracellular responses of the Muller (glial) cells of mudpuppy retina: their relation to b-wave of the electroretinogram. J Neurophysiol. 1970;33:323-341.

(Continued)

*Primary Examiner* — Kevin W Weddington
(74) *Attorney, Agent, or Firm* — Norton Rose Fulbright Canada; Marie-Helene Rochon

(57) ABSTRACT

The present disclosure concerns the use of a phosphodiesterase inhibitor, such as, for example, sildenafil, to repair a brain and/or a retinal injury in a newborn. The phosphodiesterase inhibitor can be used in a premature or a term baby that has been exposed to hyperoxia or hypoxia which caused a brain and/or a retinal injury.

17 Claims, 7 Drawing Sheets

(56) References Cited

PUBLICATIONS

Stockton RA, Slaughter MM. B-wave of the electroretinogram. A reflection of ON bipolar cell activity. J Gen Physiol. 1989;93:101-122.

Jung S, Polosa A, Lachapelle P, Wintermark P. Visual Impairments Following Term Neonatal Encephalopathy: Do Retinal Impairments Also Play a Role? Invest Ophthalmol Vis Sci. 2015;56:5182-5193.

Li B, Barnes GE, Holt WF. The decline of the photopic negative response (PhNR) in the rat after optic nerve transection. Doc Ophthalmol. 2005;111:23-31.

Machida S, Raz-Prag D, Fariss RN, Sieving PA, Bush RA. Photopic ERG negative response from amacrine cell signaling in RCS rat retinal degeneration. Invest Ophthalmol Vis Sci. 2008;49:442-452.

Shaikh H, Lechpammer M, Jensen FE, Warfield SK, Hansen AH, Kosaras B, Takeoka M, Poduri A, Madsen JR, Bergin AM, Whalen S, Jensen FE: Increased brain perfusion persists over the first month of life in term asphyxiated newborns treated with hypothermia: Does it reflect activated angiogenesis? Transl Stroke Res 2015; 6: 224-33.

* cited by examiner

☐ Sham vehicle ☐ HI vehicle ▨ HI 10 mg/kg
▨ HI 2 mg/kg ■ HI 50 mg/kg

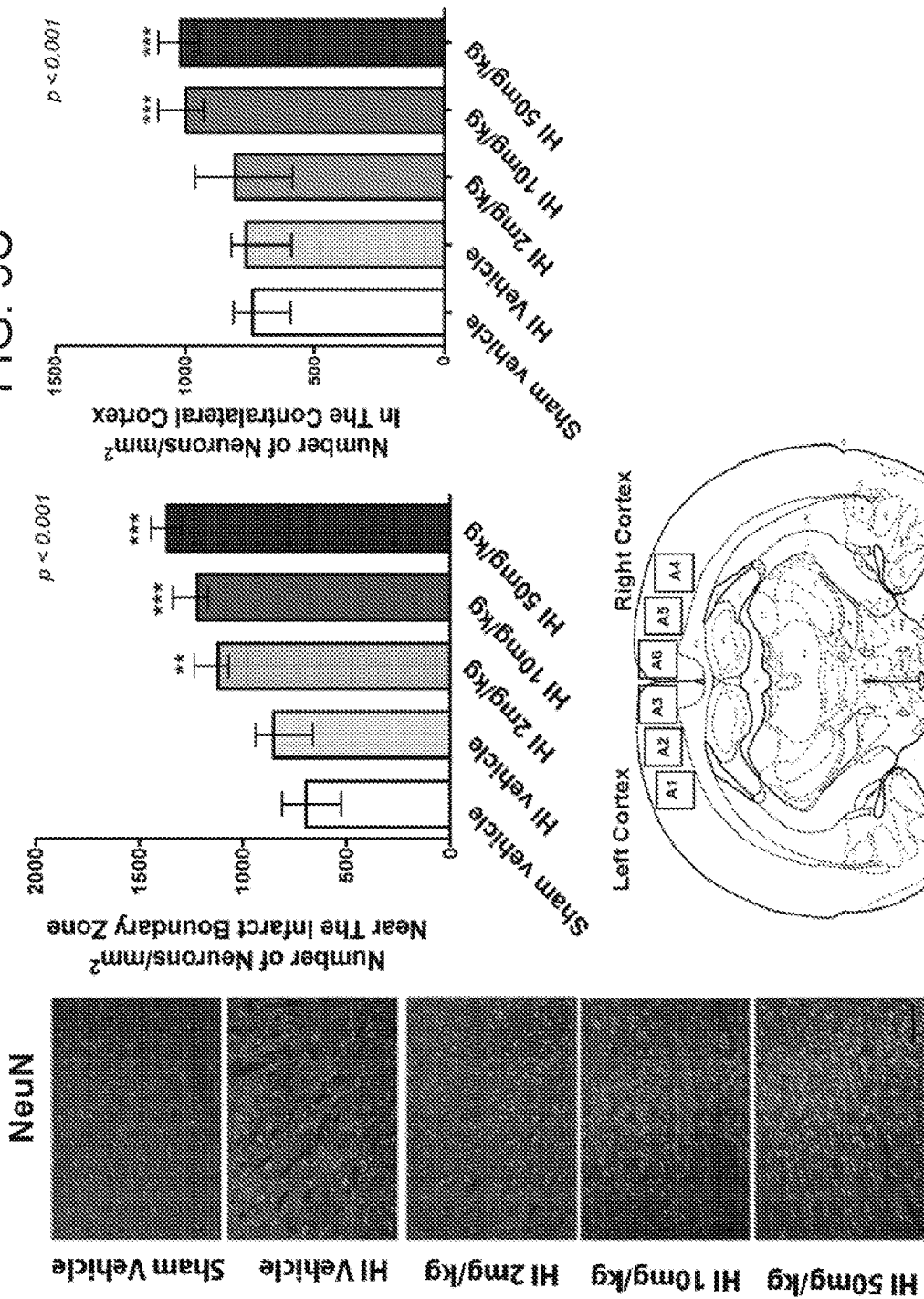
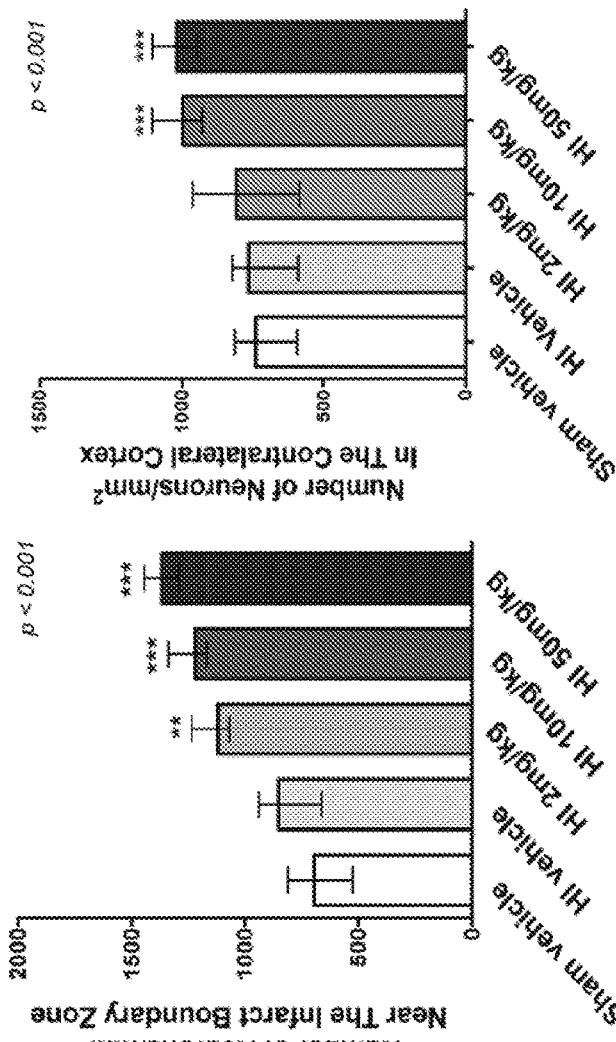
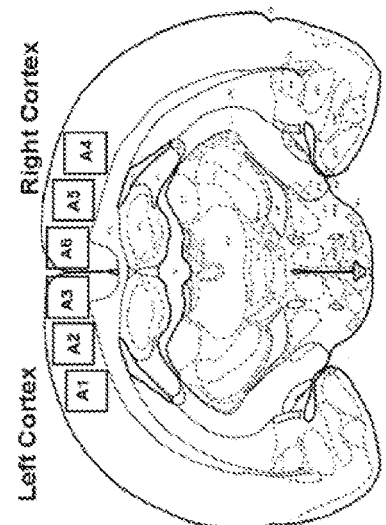

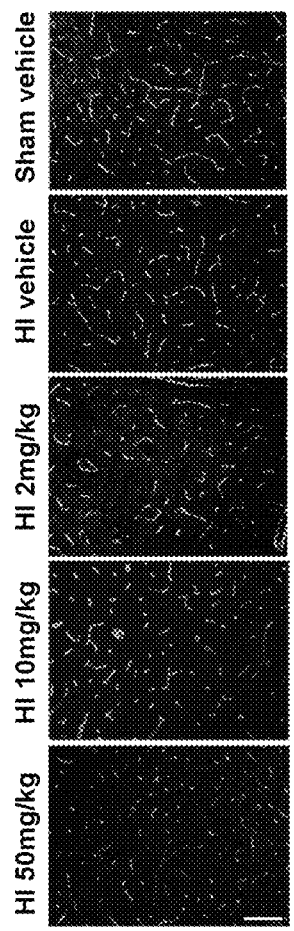
Fig. 4A Collagen IV
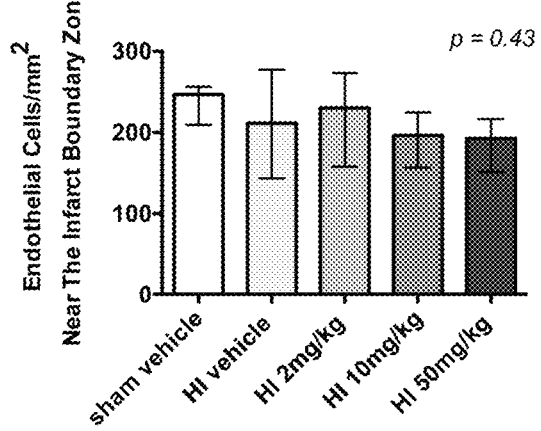
Fig. 4B Lectin
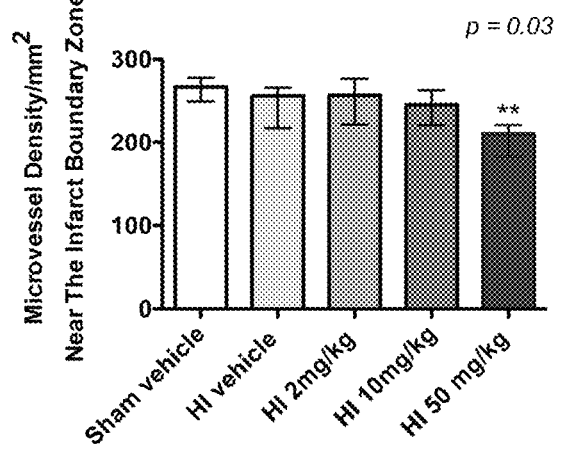
Fig. 4C Collagen IV

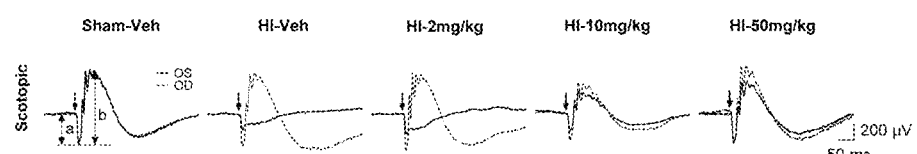
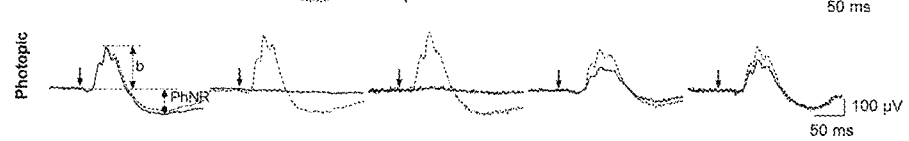
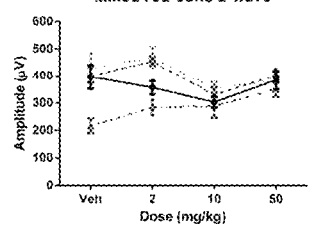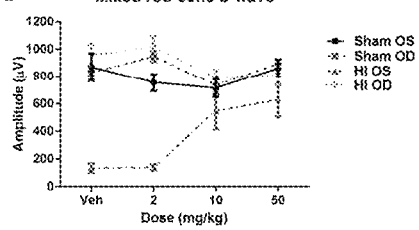
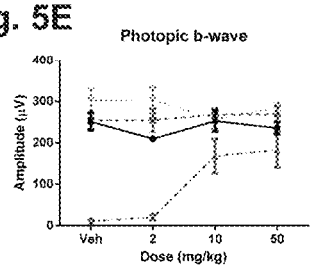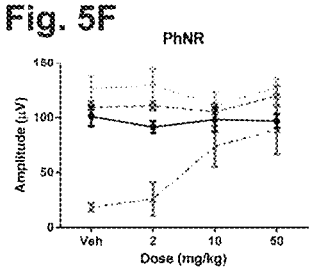

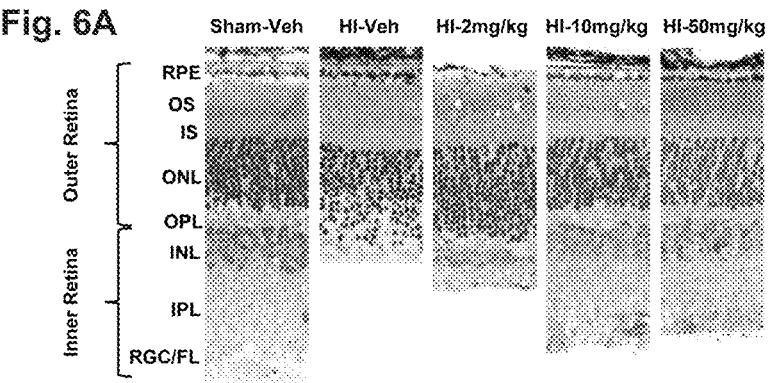
Fig. 6A
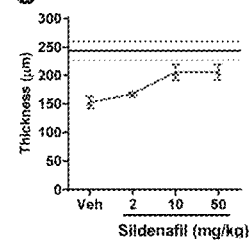
Fig. 6B1 Total
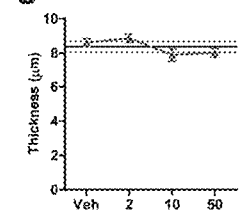
Fig. 6B2 RPE
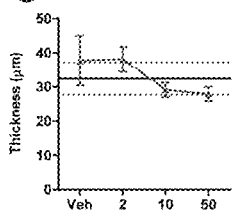
Fig. 6B3 OS
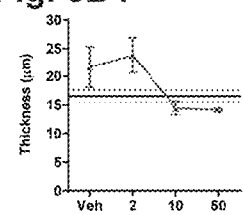
Fig. 6B4 IS
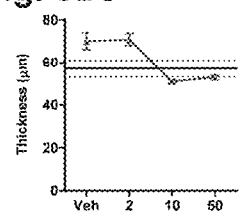
Fig. 6B5 ONL
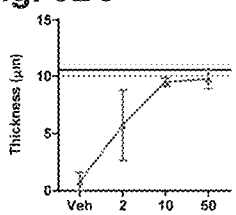
Fig. 6B6 OPL
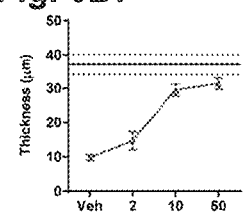
Fig. 6B7 INL
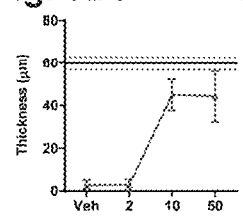
Fig. 6B8 IPL
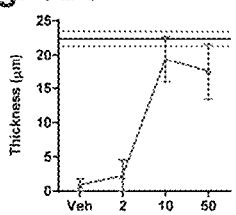
Fig. 6B9 RGC/FL

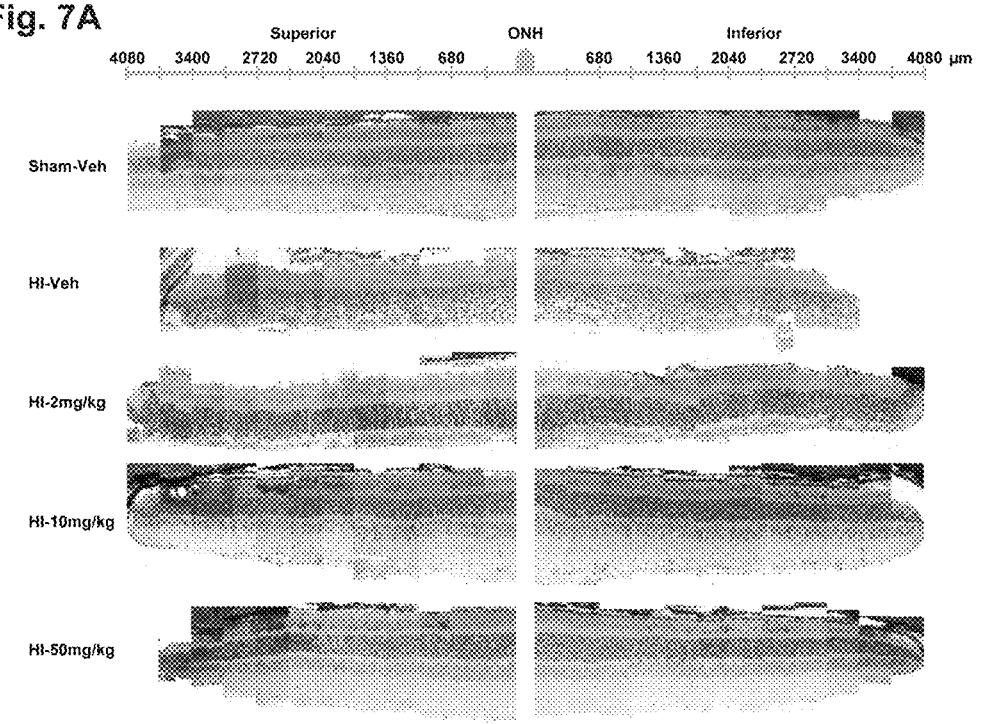
Fig. 7A
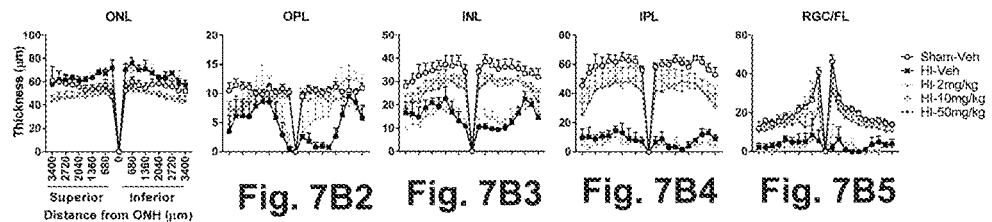
Fig. 7B1  Fig. 7B2  Fig. 7B3  Fig. 7B4  Fig. 7B5

PHOSPHODIESTERASE INHIBITORS TO REPAIR BRAIN AND/OR RETINAL INJURY IN HUMAN NEWBORNS

CROSS-REFERENCE TO RELATED APPLICATIONS AND DOCUMENTS

This application claims priority from U.S. provisional patent application 62/372,860 filed on Aug. 10, 2016. The content of the priority application is herewith incorporated herewith in its entirety.

TECHNOLOGICAL FIELD

The present application relates to the treatment and repair of a brain and/or a retinal injury, caused by the exposure to hyperpoxia or hypoxia, in a human newborn.

BACKGROUND

Exposure of human newborn to hyperoxia or hypoxia leads to brain and retinal injuries. For example, birth asphyxia in newborns remains a serious condition causing significant mortality and long-term morbidity, including cerebral palsy, intellectual disabilities and blindness. Treatments, such as hypothermia, have been developed to protect the brain and retina and prevent further injury after hypoxia.

However, none of the currently available or developing therapies intend to repair the brain or retinal injury caused by hypoxia or hyperoxia in premature and term babies. Neurorestorative treatments of brain and retinal injuries have not been explored in newborns. Therefore, there is a need to develop additional therapies to repair brain and/or retinal injuries in newborns that have undergone hyperoxia or hypoxia in order to improve functional and structural recovery of the already damaged brain and/or retina.

BRIEF SUMMARY

The present disclosure concern the use of phophodiesterase inhibitor for the treatment of a newborn having a brain and/or a retinal injury caused by an exposure to hyperoxia or hypoxia.

In an aspect, the present disclosure provides a method for treating a brain and/or a retinal injury caused by an exposure to hyperoxia or hypoxia in a newborn in need thereof. Broadly, the method comprises administering a therapeutically effective amount of a phosphodiesterase inhibitor or a pharmaceutically acceptable salt thereof to the newborn so as to treat the brain and/or the retinal injury. In an embodiment, the phosphodiesterase inhibitor is a selective phosphodiesterase inhibitor, such as, for example, a phosphodiesterase type 5 selective inhibitor. In some additional embodiments, the phosphodiesterase type 5 selective inhibitor is sildenafil which can, for example, be provided as a citrate salt or as a suspension of the citrate salt. In another embodiment, the phosphodiesterase inhibitor is administered orally. In another embodiment, the phosphodiesterase inhibitor is administered twice daily. In a yet another embodiment, the phosphodiesterase inhibitor is administered at a dosage of from 2 mg/kg to 50 mg/kg. In still yet another embodiment, the phosphodiesterase inhibitor is administered during 7 consecutive days following the onset of the brain and/or the retinal injury. In a further embodiment, the phosphodiesterase inhibitor is first administered at least 12 hours after the onset of the brain and/or the retinal injury. In still a further embodiment, the newborn, which can be a human baby, is a premature baby or a term baby. In some embodiments, the method is for treating the brain injury. In other embodiments, the method is for treating the retinal injury. In another embodiment, the injury is caused by hyperoxia. In a further embodiment, the injury is caused by hypoxia.

BRIEF DESCRIPTION OF THE DRAWINGS

Having thus generally described the nature of the disclosure, reference will now be made to the accompanying drawings, showing by way of illustration, a preferred embodiment thereof, and in which:

FIGS. 3A to 3D illustrate immunostaining results for neurons in HI and sham rat pups treated with sildenafil or vehicle. (A) Representative immunofluorescent micrographs of the mature neurons labeled with NeuN near the infarcted cortical zone (scale bar=100 μm). (B) Neuronal cells were counted in three fields of view near the infarcted cortical zone (median with IQR). (C) Neuronal cells were counted in three fields of view in the corresponding region of the contralateral (right) cortex (median with IQR). The result identified with  and * correspond to p<0.01, *p<0.001, significant for comparisons vs. sham vehicle rat pups. Kruskal-Wallis test with Dunn's post hoc comparison tests. (D) Schematic of ipsilateral cortical zone near infarct boundary (A1-A3) and the corresponding contralateral cortical zone where neurons were counted (A4-A6).

FIGS. 4A to 4C illustrate immunostaining results for endothelial cells in HI and sham rat pups treated with sildenafil or vehicle (scale bar=100 μm). (A) Representative immunofluorescent micrographs of the endothelial cells, demonstrated by labeling for the lectin-stained blood vessels. (B) Endothelial cells, labeled by lectin staining, were counted in three fields of view near the infarcted cortical zone (median with IQR). (C) Microvessel density, labeled by collagen IV staining, was measured in three fields of view near the infarcted cortical zone (median with IQR). The result identified with  correspond to p<0.01, significant for comparisons vs. sham vehicle rat pups; Kruskal-Wallis test with Dunn's post hoc comparison tests.

FIGS. 5A to 5F illustrate flash electroretinograms of the sham and HI rat pups treated with different doses of sildenafil: 2 mg/kg, 10 mg/kg, and 50 mg/kg. (A, B) Representative scotopic (A) and photopic (B) electroretinograms (ERG) waveforms obtained from the left (i.e., ipsilateral to the carotid ligation) (solid line) and right (i.e., contralateral to the carotid ligation) (dashed line) eyes. Vertical arrows denote the stimulus onset. Double-headed arrows display how the amplitudes were measured. The units of horizontal and vertical scale bars are, respectively, in milliseconds and microvolts. (C-F) Amplitude measurements of the ERG waves of sham-treated animals (● Sham ipsilateral left eye, OS; ■ Sham contralateral right eye, OD) and animals submitted to HI (▲ HI OS ▼ HI OD). Mean±standard error, SE. (C) Mixed rod-cone a-wave amplitude. (D) Mixed rod-cone b-wave amplitude. (E) Photopic b-wave amplitude. (F) Photopic negative response (PhNR) amplitude.

FIGS. 6A and 6B illustrate the retinal structure in the left eyes of the sham vehicle rat pups and the HI rat pups treated with different doses of sildenafil: 2 mg/kg, 10 mg/kg, and 50 mg/kg. (A) Representative toluidine blue-stained retinal cross sections (magnification: 403). Images were taken at 1000 lm inferior to the optic nerve head. (B) Thicknesses of the different retinal layers. Solid horizontal line represents the mean of the sham vehicle group; dashed horizontal lines represent the Standard Error of the Mean (SEM) of the sham vehicle group. Mean±SE.

FIGS. 7A and 7B illustrate topographic distribution of the inner retinal injury in the left eyes of the sham vehicle rat pups and the HI rat pups treated with different doses of sildenafil: 2 mg/kg, 10 mg/kg, and 50 mg/kg. (A) Reconstruction of the retina along the superior-inferior axis at the level of the ONH (magnification: 403). (B) Spider graphs representing the thickness of retinal layers with respect to eccentricity. Mean±SE.

DETAILED DESCRIPTION a) Definitions

Figure 1A:
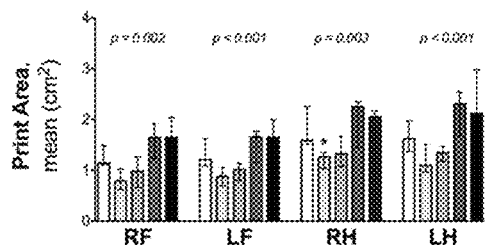
FIGS. 1A to 1E illustrate the significant gait parameters in Hypoxia-Ischemia (HI) and sham rat pups treated with sildenafil or vehicle. RF=Right forelimb; LF=left forelimb; RH=right hindlimb; LH=left hindlimb. (A) Print area. (B) Maximum contact area. (C) Print length. (D) Initial dual stance duration. (E) Terminal dual stance duration. Median with IQR values are presented. The result identified with * correspond to p<0.05, significant for comparisons vs. sham vehicle rat pups. Kruskal-Wallis test with Dunn's post hoc comparison tests.
Figure 1B:
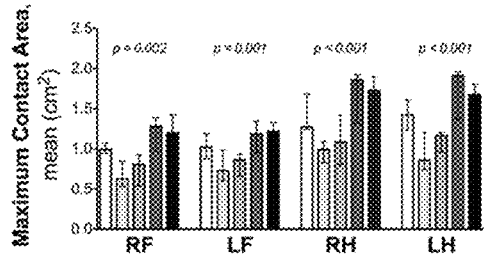
Figure 1C:
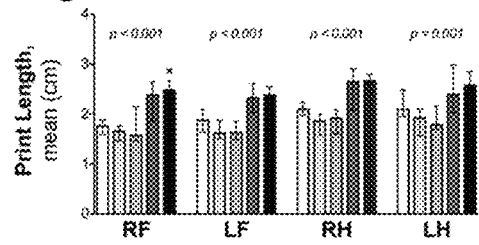
Figure 1D:
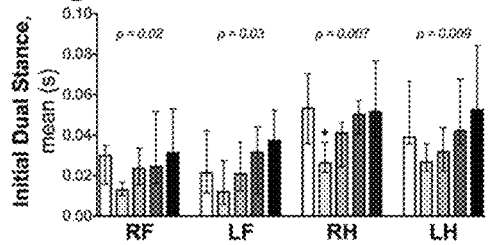
Figure 1E:
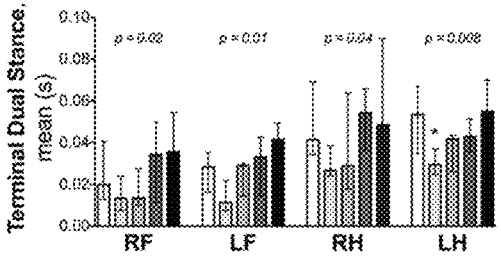

Throughout this text, various terms are used according to their plain definition in the art. However, for purposes of clarity, some specific terms are defined below.

Hyperoxia. Hyperoxia is the exposure to oxygen leading to excessive oxygen saturation in the blood. In some embodiments, hyperoxia can be caused by an exposure to a gas having more than 21% oxygen. The cells, tissues and organs that are exposed to an excess supply of oxygen can be damaged by oxygen toxicity. Hyperoxia can for example be caused when oxygen therapy is provided to support the lungs of premature newborns. Such oxygen therapy often leads to damages to the brain called encephalopathy of prematurity (EOP) and to the retina called retinopathy of prematurity (ROP) and long-term neurodevelopmental sequelae and visual impairments. In the context of the present disclosure, an "injury caused by exposure to hyperoxia" is a biological damage to the brain and/or the retina which occurred after the exposure to hyperoxia and was triggered, at least in part, by exposure to hyperoxia.

Hypoxia. Hypoxia is the exposure to oxygen leading to a below-normal level of oxygen in the blood. In some embodiments, hypoxia can be caused by an exposure to a gas having less than 21% oxygen. For example, in neonatal care, birth asphyxia, also referred sometimes to neonatal hypoxia-ischemia, leads to insufficient blood flow to a tissue, such as the brain and the retina. Birth asphyxia can trigger neonatal encephalopathy and is a major cause of mortality and long-term neurological impairments in surviving infants. Asphyxiated newborns can also develop long-term neurological complications (including visual impairments) due to injuries to their brain and retina. Neonatal encephalopathy remains a major cause of mortality and morbidity worldwide. Neonatal encephalopathy often leads to chronic activation of inflammatory cascades that hinders repair of the developing brain. Neonatal encephalopathy can also lead to severe white matter injury that hinders repair of the developing brain and leads to long-term neurological impairments. It has been shown that microgliosis and astrogliosis are activated by hypoxia-Ischemia (HI). Hippocampus and cerebellum are also well-documented sites of neuronal injury in neonatal HI. In the context of the present disclosure, an "injury caused by exposure to hypoxia" is a biological damage to the brain and/or the retina which occurred after the exposure to hypoxia and was triggered, at least in part, by exposure to hypoxia.

Hypoxia-ischemia (HI). This term refers to the reduction of blood flow and/or oxygen to cells, tissues and organs so that the concentration of blood and/or oxygen is not sufficient to maintain the normal function of the cells and organs. Prolonged hypoxia-ischemia can lead to ischemic attack, brain infarction, i.e. tissue necrosis in diverse areas of the brain, and other conditions. In human babies, the term neonatal encephalopathy is used to refer to HI.

Inflammatory condition, disease or disorder. As used herein, these terms collectively refer to a dysregulated inflammatory response which causes a pathological cellular destruction of tissues in an afflicted individual. The inflammation can either be acute or chronic. Inflammatory conditions include, but are not limited to neonatal encephalopathy. The methods and therapeutic uses described herein can be used to reduce inflammation of an injury caused by hyperoxia or hypoxia.

Newborn. As used herein, this term refers to a baby following its birth. A newborn can be a premature baby, or a term baby. In humans, a baby is usually considered "premature" when born before 37 complete weeks of gestation from the first day of the last menstrual period. In contrast a "term baby" is known as an infant born beyond 37 weeks of gestation from the first day of the last menstrual period. The weeks of gestation can be also be determined by ultrasound dating or by counting from the day of implantation. The perinatal period of the newborn refers to the first 28 days of life of such baby.

Pharmaceutical composition. As used herein, this term means therapeutically effective amounts (dose) of the agent together with pharmaceutically acceptable diluents, preservatives, solubilizers, emulsifiers, adjuvants and/or carriers.

Therapeutically effective amount. This expression refers to an amount (dose) effective in mediating a therapeutic benefit to a subject (for example prevention, treatment and/or alleviation of symptoms of cancer). It is also to be understood herein that a "therapeutically effective amount" may be interpreted as an amount giving a desired therapeutic effect, either taken in one dose or in any dosage or route, taken alone or in combination with other therapeutic agents.

Pharmaceutically acceptable carrier. This term refers to an acceptable carrier or adjuvant that may be administered to a patient, together with a compound of this disclosure, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Pharmaceutically acceptable salt. This expression refers to conventional acid-addition salts or base-addition salts that retain the biological effectiveness and properties of the therapeutic agent described herein. They are formed from suitable non-toxic organic or inorganic acids or organic or inorganic bases. Sample acid-addition salts include those derived from inorganic acids such as hydrochloric acid, hydrobromic acid, hydroiodic acid, citric acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as e.g., tetramethylammonium hydroxide. The chemical modification of an agent into a salt is a well-known technique which is used in attempting to improve properties involving physical or chemical stability, e.g., hygroscopicity, flowability or solubility of compounds.

b) Phosphodiesterase Inhibitors

The present disclosure provides the use of phosphodiesterase inhibitors to repair a brain and/or a retina injury caused by an exposure to hyperoxia or hypoxia in a newborn. The present disclosure therefore provides the use of phosphodiesterase inhibitors as a treatment to an existing injury. It is contemplated that the present disclosure is not a measure intending to prevent or protect the cells and organs suspected to be submitted to hypoxia or hyperoxia occurs. The present disclosure concerns the use of phosphodiesterase inhibitors for treating newborns having (brain and/or retina) injuries in an attempt to repair the structure of damaged cells and organs caused by the hyperoxia or hypoxia, and to restore, at least in part, their function.

Without wishing to be bound to theory, it is believed that the phosphodiesterase inhibitor has the ability to improve neurological deficits. For example, it is contemplated that the phosphodiesterase inhibitor can decrease brain injury following term neonatal hypoxia-ischemia (e.g., suspected or confirmed newborns afflicted by neonatal encephalopathy). In addition, the phosphodiesterase inhibitor administered after hypoxia-ischemia may repair brain injury in the cerebrum and may, in some embodiments, also have some beneficial impact on the cerebellum. Therefore, it is contemplated that the phosphodiesterase inhibitor can have the ability to modulate neuroinflammation following hypoxia-ischemia in a newborn as defined herein. In some embodiments, the phosphodiesterase inhibitor can also increase oligodendrocyte progeny in the ischemic brain of middle-aged. The phosphodiesterase inhibitor may therefore have the ability to improve the myelination capability by increasing oligodendrogenesis following hypoxia-ischemia. It is further believed that, in some embodiments, the phosphodiesterase inhibitor can have the ability to reduce the infarct size. The total brain size can also be improved by the action of the phosphodiesterase inhibitor. In some embodiments, the phosphodiesterase inhibitor can lead to an increase in neuronal number near the infarct boundary zone in the cortex.

In some embodiments, the phosphodiesterase inhibitor can also improve the retinal function outcome as well as improve the retinal structure outcome in HI-afflicted subjects. More particularly, the phosphodiesterase inhibitor may have the ability to improve the thicknesses of the layers (total retina, ONL, OPL, INL, IPL, RGC/FL) affected in subjects having been exposed to hypoxia.

In addition, without being bound to theory, it is contemplated that the phosphodiesterase inhibitor does not impact normal brain growth and has the ability to enhance the brain repair processes in an injured brain, which lead to an improved functional and structural recovery. In some embodiments, the phosphodiesterase inhibitor does not impair the treated subject's body weight and does not cause more death. Furthermore, the phosphodiesterase inhibitor is safe to use in humans and newborns, including premature babies.

The phosphodiesterase inhibitor disclosed herein is a compound that prevent the action of one or more of the five subtypes of the enzyme phosphodiesterase (PDE). The inactivation of the intracellular second messengers cyclic adenosine monophosphate (cAMP) and cyclic guanosine monophosphate (cGMP) by said PDE subtypes is then inhibited. In the context of the present disclosure, the PDE inhibitor can be a non-selective PDE inhibitor or a selective PDE inhibitor. In embodiments in which, the PDE inhibitor is a selective PDE inhibitor, the PDE selective inhibitor can be a PDE1 selective inhibitor, a PDE2 selective inhibitor, a PDE3 selective inhibitor, a PDE4 selective inhibitor or a PDE5 selective inhibitor.

The phosphodiesterase inhibitor disclosed herein can be a phosphodiesterase type 5 selective inhibitor, and can therefore block the action of cGMP-specific phosphodiesterase type 5 (PDE5) on cyclic GMP. For example, the phosphodiesterase inhibitor can be one of sildenafil, avanafil, iodenafil, mirodenafil, tadalafil, vardenafil, udenafil, zaprinast, icariin and its synthetic derivatives, benzamidenafil or dasantafil.

In a particular embodiment, the phosphodiesterase inhibitor is sildenafil. Sildenafil is known as a vasodilator that acts by inhibiting the phosphodiesterase type-5 (PDE5) enzyme, which breaks down cyclic guanosine monophosphate (cGMP).

The phosphodiesterase inhibitor can also be used in form of one of its pharmaceutically acceptably salt, as described herein. For example, the phosphodiesterase inhibitor can be a citrate salt of sildenafil, such as Viagra® sildenafil citrate.

The phosphodiesterase inhibitor can be provided as pharmaceutical compositions comprising therapeutically effective amount of the phosphodiesterase inhibitor or pharmaceutically acceptable salt thereof, and a pharmaceutically acceptable carrier, as described herein.

Suitable methods of administering the phosphodiesterase inhibitor and corresponding compositions are available and well known to those of skill in the art, and, although more than one route can be used to administer a particular composition, a particular route can often provide a more immediate and more effective reaction than another route. The therapeutic agents disclosed herein may be administered, either orally or parenterally, systemically or locally. The compositions used in the methods of the present disclosure are preferably administered orally; sublingually; or buccally, and as such can be in the form of tablets, capsules, granules, powders or an (USP) solution. The phosphodiesterase inhibitors may also be administered by the intravenous route.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compositions with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use. Solution such as Ora-Sweet® and Ora-Plu® suspending vehicle can be used for example.

The compositions of the present disclosure may be employed alone or in combination with other suitable therapies or therapeutic agents useful in the treatment of brain and/or retina injuries. For example, the phosphodiesterase inhibitor can also be used in combination with therapeutic hypothermia.

The present disclosure also provides kits comprising the pharmaceutical compositions described herein as well as instructions on how to use or administer the therapeutic agents.

c) Method of Treating and Therapeutic Uses

The present disclosure provides a method for treating a brain and/or a retinal injury caused by an exposure to hyperoxia or hypoxia in a newborn. The immature neonatal brain cannot simply be considered as a "small" adult brain, since it is still maturating at the time of birth, with ongoing connectivity processes, myelination, vasculogenesis and angiogenesis. Consequently, the mechanisms underlying neonatal brain injury are most probably unique compared to those underlying adult stroke. In addition, brain inflammation appears as an additional contributor to brain injury in these newborns. As previously mentioned, the present method is intended to repair injuries that have occurred due to hypoxia or hyperoxia and to restore the cells and organs function. The present method is not a prevention or protection method and is intended to be used to mitigate an existing brain and/or retina injury.

In some optional embodiments, before treating the brain and/or retina, the presence of an injury can be assessed using observations and detection techniques. For example, the brain and/or the retina of the newborn can be examined using brain imaging (such as brain magnetic resonance imaging, head ultrasound and/or computed tomography) and retinal tests (such as electroretinogram, visual evoked potential, optical coherence tomography and/or retinal photography). It is understood that identification of the brain and/or retina injury is optional. Indeed, damages are most likely to occur after exposure to hyperoxia or hypoxia. In such embodiment, the phosphodiesterase can be used only in subjects with suspected or proven brain and/or a retina injury.

The method comprises administering a therapeutically effective amount of a phosphodiesterase inhibitor or a pharmaceutically acceptable salt thereof to the newborn so as to treat the brain and/or the retinal injury. The method therefore comprises administering the pharmaceutical composition as described herein. The present disclosure also comprises using a therapeutically effective amount of a phosphodiesterase inhibitor or a pharmaceutically acceptable salt thereof (alone or in the form of a pharmaceutical composition) in the newborn so as to treat the brain and/or the retinal injury.

In some embodiments, the phosphodiesterase inhibitor or a pharmaceutically acceptable salt thereof (or the corresponding pharmaceutical composition comprising same) is first administered only after the onset of an injury. For example, the phosphodiesterase inhibitor can be first administered at least (and in embodiments, not before) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours after exposure hypoxia and hyperoxia. As used in the context of the present disclosure, a "first administration" of the phosphodiesterase inhibitor refers to the first use of the phosphodiesterase inhibitor in the newborn. This delay can take into consideration the time that it would take to identify those human newborns at risk of brain and/or retina injury. The phosphodiesterase inhibitor is administered to a newborn, preferably during the onset of treatment is during the perinatal period.

The effective amount of phosphodiesterase inhibitor to be administered may be determined by one of ordinary skill in the art, and includes exemplary pharmaceutical dosage amounts of from about 2 to 50 mg/kg or from 0.5 to 3 mg/kg (such as, for example, 2 mg/kg) of body weight of phosphodiesterase inhibitor. In some embodiments, the dosage amount is administered twice per day. However, the dosage amount of phosphodiesterase inhibitor can be administrated more than twice per day. The phosphodiesterase inhibitor can also be administrated as a single dose. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combination, and severity of the particular condition.

In some embodiments, the phosphodiesterase inhibitor or a pharmaceutically acceptable salt thereof is administrated during at least 2, 3, 4, 5, 6, 7, 8, 9 or 10 consecutive days. The phosphodiesterase inhibitor is preferably administered during the perinatal period of the newborn. While the treatment can start in the perinatal period, it is contemplated that at the end of the treatment period, the baby may no longer be considered to be in the perinatal period. In some embodiments, the phosphodiesterase inhibitor or a pharmaceutically acceptable salt thereof is administrated on the first day of treatment and release of the phosphodiesterase inhibitor extended over at least 2, 3, 4, 5, 6, 7, 8, 9 or 10 consecutive days.

The method of treating brain and/or retinal injuries of the present disclosure comprises repairing brain and/or retinal injuries. More particularly, treating brain and/or retinal injuries results from an increase in cGMP in the brain and/or retina of the premature and term newborn.

The method of the present disclosure can be used to treat a brain injury. In some embodiments, treating brain injuries results in an increase of number of neurons and/or a decrease of inflammation in the brain, an increase in mature oligodendrocytes in the white matter, an improvement in neuron myelination, an improvement in the overall thickness of the layers of the cerebellum, a reduction in VEGF expression in brain astrocytes, a reduction in the number of activated microglia and/or a reduction in the number or reactive astrocytes. Treating brain injuries can also comprise enhancing the brain repair processes to improve functional and structural recovery.

The method of the present disclosure can be used to treat a retina injury. In some embodiments, treating retinal injuries results in improved retinal function, and improved retinal structure. The treatment of the retina injury can cause a decrease in retina inflammation (for example by reducing the number of astrocytes), an improvement of the retina cells (for example restoring the number of retinal ganglion cells and bipolar cells), an improvement in scotopic amplitude and/or an improvement in photopic b-wave amplitude.

The methods of the present disclosure can also be used to treat a brain injury and a retina injury.

The present disclosure will be more readily understood by referring to the following examples, which are given to illustrate the disclosure rather than to limit its scope.

EXAMPLE

Example 1: Use of Sildenafil to Improves Brain Injury Recovery 1.1 Animals

The experiments were conducted in accordance with the standard operating procedures for the use of animals in research as per the guidelines in the Canadian Council on Animal Care's Guide to the Care and Use of Experimental Animals, and in the Animals for Research Act. These experiments were approved by the local Animal Care Committee from the Montreal Children's Hospital, McGill University Health Centre. Adult female Long-Evans rats with their male-only litters (Harlan Laboratories) were received in the animal facility, housed under standard environment, and allowed food and water ad libitum. Rat pups remained with their mother until weaning at postnatal day 21 (P21). Rats were monitored daily by animal facility health care technicians, and additionally by the researchers during the course of the study.

1.2 Induction of Term Neonatal Hypoxic-Ischemic Encephalopathy (HIE)

A well-established Vannucci rat model of term neonatal HIE, which combined a left common carotid artery ligation and a 2 hour exposure to hypoxia (8% oxygen) in 10-day-old (P10) rat pups, was used for the experiments, since this model is generally recognized to mimic the brain injuries observed in human term asphyxiated newborns. Briefly, the 10-day-old male Long-Evans rat pups were weighed and then deeply anesthetized with an intraperitoneal injection of fentanyl (0.2 mg/kg) and midazolam (1 mg/kg) to the point of unresponsiveness to noxious stimulation. Lidocaine-prilocaine cream (EMLA®; AstraZeneca Inc.) was applied to the ventral neck skin 30 minutes before surgery. The skin was cleaned with 2% chlorhexidine solution followed by 70% alcohol. A vertical incision was made along the ventral surface of the neck. The left common carotid artery was located, isolated, and then ligated with a single tight suture. Following the unilateral ligation, the skin incision was closed with an adhesive (n-butyl cyanoacrylate; 3 M Vet-Bond Tissue Adhesive®; 3 M USA). The anesthesia was reversed with an intraperitoneal injection of naloxone (0.1 mg/kg) and flumazenil (1 mg/kg). Before injecting intraperitoneally, it was always checked that blood or fluid was not coming back in the syringes and no complications related to bowel perforation was noticed. For each rat pup, anesthesia time and surgical time were kept to a minimal time of less than 5-10 minutes. The pups were allowed to recover for approximately 1.5 h after surgery and then were placed in a sealed hypoxia chamber (Plastic Concepts, North Billerica, USA). The sealed chamber was infused with nitrogen until a level of 8% oxygen was reached, which was maintained for 2 h (oxygen analyzer model 600, Engineered Systems & Designs, Newark, Del.). The pups were allowed to recover for 30 minutes and then were returned to their cages with the mother. The rats undergoing the whole procedure were considered as the hypoxic-ischemic (HI) group (n=10-12 animals/groups). Sham operated rat pups (identical procedure as the HI group, but not the ligation and hypoxia) served as the control group (n=10-12 animals/groups). The sample size of the current study was a sample size of convenience, subject to restrictions imposed by the institutional ethics committee that reviewed it, and based on the principles of the 3Rs (replacement, reduction, and refinement). Sham rat pups received the same sedation as HI rat pups permitting to control for the effect of sedation on the brain. Normal body temperature of both sham and HI rat pups, while they were separated from the mother, was maintained during the whole procedure (i.e., surgery±hypoxia) using warming blankets (Cincinnati Sub-Zero, Cincinnati, USA).

1.3 Sildenafil Preparation and Administration 100 mg tablets of Viagra® (Pfizer) were crushed in a pestle and mortar and ground to an ultra-fine powder. The fine powder was suspended in a 50/50 blend of sterile water and Ora-Blend® suspension media (vehicle) (Perrigo), resulting in a 50 mg/ml stock.

HI and sham operated rat pups were weighed every day and then randomized to sildenafil or vehicle twice daily by oral gavage, starting from 12 hours post-HI for 7 consecutive days from P10 to P17. Different doses of sildenafil were used in the HI and sham operated rat pups to assess whether the effect of sildenafil could be dose-dependent: i.e., a low dose (2 mg/kg), a medium dose (10 mg/kg), and a high dose (50 mg/kg) of sildenafil (n=11-12 animals in each group).

1.4 Weight

Animals were weighed the day of the surgery on P10, then daily while receiving sildenafil or vehicle from P10 to P17, and then again on P21, P27, and P29.

1.5 Functional Testing

To assess the neurological deficits induced by hypoxic-ischemic and the potential recovery with sildenafil treatment, the rat pups were subjected to gait assessment before being euthanized, using the CatWalk automated gait analysis system (Noldus Information Technology, Wageningen, The Netherlands). The experiments were run in a dark environment (below 20 lux of illumination). The equipment consists of a 1.3 m-long glass plate with a dim fluorescent light coming from the side and beamed into the glass. The light reflected downwards by the rats' paws as they contact the glass floor is captured by a high-speed video camera placed under the walkway, and then transformed into a digital image (Hamers F P T et al., 2006; Hetze S et al., 2012; Lubjuhn J et al., 2009, Parkkinen S et al., 2013, Wang Y et al., 2008). The walkway was 90 mm wide. The camera was positioned 40 cm below the walkway, and automatic detection settings were applied. The rat pups walked spontaneously at their own speed; the mother was systematically placed in the goal box to motivate the rat pups to run towards it. An intensity threshold was set to 0.1, the camera gain was set to 20, and the maximum allowed speed variation was set to 60%. A minimum of three quality runs per rat pups were acquired. Only uninterrupted runs were saved for analysis; runs, where animals turned or walked backwards, were excluded, and the animal got another try.

One investigator, who was blind to the treatment group subdivision, performed the gait analysis. During the data analysis, the steps were automatically labeled as right fore paw (RF), left fore paw (LF), right hind paw (RH), and left hind paw (LH), in which the left stands for the non-impaired side and the right for the impaired side. Faulty labels caused by tail, whiskers, or genitalia were removed (Lubjuhn J, et al., 2009). After the identification and labeling of the individual footprints, a wide range of gait data was generated, including (1) spatial parameters related to individual paws (maximum intensity, maximum contact area, print area, print length, and print width); (2) relative spatial relationship between different paws (base of support, initial dual stance, terminal dual stance, and stride length); (3) interlimb coordination (step sequence regularity index); and (4) temporal parameters (swing duration, stance duration, and cadence), as previously described in other studies (Hamers F P T et al., 2006; Hetze S et al., 2012; Lubjuhn J et al., 2009, Parkkinen S et al., 2013, Wang Y et al., 2008). The definitions for the gait parameters were similar to the those previously described (Hetze S et al., 2012; Parkkinen S et al., 2013, Wang Y et al., 2008). Maximum intensity is the average intensity of the print at the moment of maximal contact; it is an indication of paw pressure. Maximum contact area is the size of the print area at maximal contact. Print area is the area of the complete print, including all frames during the stance phase. Print length is the length of the complete print. Print width is the width of the complete print. Base of support is the distance between the mass-midpoints of the prints at maximal contact. Initial dual stance is a measure of initial postural positioning, defined as the duration of the first time in a step cycle of a paw that the contralateral paw also makes contact with the walking surface. Terminal dual stance is a measure of final postural positioning, defined as the duration of the second time in a step cycle of a paw that the contralateral paw also makes contact with the walking surface. Stride length is the distance between consecutive steps with the same paw. Step sequence regularity index is a percent index for the degree of interlimb coordination during the gait, as measured by the number of normal step sequence patterns, multiplied by the number of paws and divided by the number of paw placements. Swing duration is the duration of no contact of the paw with the walking surface in a step cycle. Stand duration is the duration of contact of the paw with the walking surface in a step cycle. Cadence is the steps that the animals walk per second.

1.6 Brain Structure

At postnatal day 30 (P30), the animals were euthanized with an intraperitoneal injection of sodium pentobarbital (100 mg/kg) and transcardially perfused with 0.1 M phosphate buffered saline, followed by 4% paraformaldehyde. The brains were extracted and post-fixed in 4% paraformaldehyde solution overnight at 4° C., and then, they were cryoprotected in 30% sucrose and serially sectioned into 16-µm coronal sections. Posterior sections were collected at −2.16 mm from Bregma (hippocampus area) for all the animals. For each animal, three slides were prepared, each of them including six posterior sections that always were collected at the same anatomical markings to enable comparisons between animals; each section was located 160 µm from the previous section.

The first slide of each animal was used to assess brain structure. After hematoxylin and eosin staining using a standard protocol, the brain morphology of the sections was examined with a light microscope (Leica DM4000B LED, Leica Microsystems, Wetzlar, Hessen, Germany) with a 5× objective. For each section, overlapping microphotographs were captured using a digital camera attached to the microscope (Leica DFC450C, Leica Microsystems, Wetzlar, Hessen, Germany). Then, these pictures were stitched together using a panoramic image stitching software (Microsoft Research Image Composite Editor) to obtain pictures of the entire coronal section. Using ImageJ (Image Processing and Analysis in Java) (Rasband W S), the surface of the left (i.e., ipsilateral to the carotid ligation) and right (i.e., controlateral to the carotid ligation) hemispheres as well total brain size (both hemispheres) were measured on two posterior sections by one investigator, who was blind to the treatment group subdivision. The two measurements were averaged to represent each animal. To remove any potential effect of individual body weight, the ratios between the left and right hemispheres were calculated and used for comparison between the different groups.

1.7 Neurons Count

Using the second slide prepared for each animal, an immunohistochemistry was performed to examine the number of mature neurons. Neurons were labeled with an anti-neuronal nuclei (NeuN) antibody (Millipore: MAB377, Billerica, Mass., USA) (dilution 1:500, incubation time 1 hour at room temperature) (Hendrickson M L et al., 2011). Sections then were incubated with the secondary antibody Alexa Fluor® 488 goat anti-rabbit IgG (Molecular Probes®, Life Technologies: A11034, Carlsbad, Calif., USA) (dilution 1:1000, incubation time 2 hours at 4° C.). These sections were rinsed with tris-buffered saline and cover slipped with Vectashield Mounting media containing 4,6-diamidino-2-phenylindole (DAPI) (Vector Laboratories: H1200, Burlingame, Calif., USA) to visualize cell nuclei. Cells co-labeled with NeuN and DAPI were identified as neurons. Two to three fields of view near the infarct boundary zone and extending in the direction of the midline of the left cortex (i.e., ipsilateral to the carotid ligation) of each of the HI animals, and three corresponding fields of view of the left cortex of the sham vehicle rat pups were assessed on two different coronal brain sections that always were collected at the same anatomical markings to enable comparisons between animals. Using an image analysis software (ImageJ) (Image Processing and Analysis in Java) (Rasband W S) that converted the scale of the original pictures to $mm^2$, the number of neurons per $mm^2$ was measured for each animal. One investigator took pictures of the respective fields of view at 10× magnification. One investigator, who was blind to the treatment group subdivision, assessed the neurons count.

1.8 Endothelial Cells Count

Using the third slide prepared for each animal, an immunohistochemistry was used to assess the endothelial cells count. Sections were labeled with lectin (biotinylated isolectin B4) (Sigma-Aldrich: L2140, St-Louis, Mo., USA) (dilution 20 µg/mL in 0.1M tris-buffered saline [pH 7.4] and 0.5% Triton X-100, incubation time 2 hours at room temperature) (Springer M L et al., 2010). To detect lectin binding, the sections were incubated with streptavidin Alexa Fluor® 350 conjugate (Molecular Probes®, Life Technologies: S11249, Carlsbad, Calif., USA) dilution 1:300 in tris-buffered saline, incubation time 2 hours at room temperature (Ndode-Ekane X E et al., 2010). Then, these sections were rinsed with tris-buffered saline and cover slipped with Vectashield Mounting media containing 4,6-diamidino-2-phenylindole (DAPI) (Vector Laboratories: H1200, Burlingame, Calif., USA) to visualize cell nuclei (Ndode-Ekane X E et al., 2010; Hallene K L et al., 2006). The endothelial cells count was assessed as per previously described methods (Hallene K L et al., 2006, Iwai M et al., 2007; Noguchi T et al., 2008; Rigau V et al., 2007; Wintermark P et al., 2013). Cells co-labeled with lectin and DAPI were identified as endothelial cells (Springer M L et al., 2010; Hallene K L et al., 2006). To estimate the density of microvessels, single immunoreactive endothelial cells were counted as individual microvessels; endothelial staining in large vessels with tunica media were disregarded in the microvessel counts (Hallene K L et al., 2006, Iwai M et al., 2007; Noguchi T et al., 2008; Rigau V et al., 2007; Wintermark P et al., 2013; Shaikh H et al., 2015). Two to three fields of view near the infarct boundary zone and extending in the direction of the midline of the left cortex (i.e., ipsilateral to the carotid ligation) of each of the HI animals, and three corresponding fields of view of the left cortex of the sham vehicle rat pups were assessed on two different coronal brain sections that always were collected at the same anatomical markings to enable comparisons between animals. Using an image analysis software (ImageJ) (Image Processing and Analysis in Java) (Rasband W S) that converted the scale of the original pictures to $mm^2$, the number of endothelial cells per $mm^2$ was measured for each animal. One investigator took pictures of the respective fields of view at 10× magnification. One investigator, who was blind to the treatment group subdivision, assessed the endothelial cells count.

In addition, using the fourth slide prepared for each animal, an immunohistochemistry with collagen IV staining also was used to assess microvessel density. Sections were labeled with an anti-collagen type IV antibody (EMD Millipore: AB769, Temecula, Calif., USA) (dilution 1:400, incubation time overnight at room temperature) (Tong X K et al., 2005). Then, these sections were incubated with the secondary antibody CyTM3-conjugated AffiniPure donkey anti-goat IgG (Cedarlane: 705-165-147, West Grove, Pa., USA) (dilution 1:400, incubation time 1 hour at room temperature). These sections were rinsed with tris-buffered saline and cover slipped with Vectashield Mounting media containing 4,6-diamidino-2-phenylindole (DAPI) (Vector Laboratories: H1200, Burlingame, Calif., USA) to visualize cell nuclei. To estimate microvessel density, single-layer immunoreactive blood vessels in all orientations were counted as individual microvessels. Collagen IV staining in large vessels with tunica media were disregarded in the microvessel counts (Hallene K L et al., 2006, Iwai M et al., 2007; Noguchi T et al., 2008; Rigau V et al., 2007; Wintermark P et al., 2013; Shaikh H et al., 2015). Two to three fields of view near the infarct boundary zone and extending in the direction of the midline of the left cortex (i.e., ipsilateral to the carotid ligation) of each of the HI animals, and three corresponding fields of view of the left cortex of the sham vehicle rat pups were assessed on two different coronal brain sections that always were collected at the same anatomical markings to enable comparisons between animals. Using an image analysis software (ImageJ) (Image Processing and Analysis in Java) (Rasband W S) that converted the scale of the original pictures to $mm^2$, the microvessel density per $mm^2$ was measured for each animal. One investigator took pictures of the respective fields of view at 10× magnification. One investigator, who was blind to the treatment group subdivision, assessed the microvessel density.

1.9 Data Analysis

For the analysis, the HI and sham rat pups were subdivided into four different treatment groups: vehicle (0 mg/kg), or sildenafil 2 mg/kg (low-dose), 10 mg/kg (medium-dose), or 50 mg/kg (high-dose). Between-group differences in outcomes were assessed for statistical significance with the Kruskal Wallis tests and pairwise comparisons were conducted to compare all treatment groups to sham vehicle control animals. A p value<0.05 was considered as statistically significant; for multiple comparisons, Dunn's post-hoc comparison tests was applied to adjust the alpha level as necessary. All statistical analyses were performed with GraphPad Prism® (GraphPad Software Inc., San Diego, Calif., USA).

1.10 Results

Sildenafil did not Impair Body Weight or Cause More Death in HI animals

No significant differences in body weight were found between the groups at P10 prior to the carotid ligation and hypoxia. However, the body weight of the HI rat pups was lower at P21, P27, and P29, compared to the sham rat pups. The different HI groups did not have any differences in body weight over time. The incidence of animal deaths was similar between the different HI groups: 3/12 died in the HI vehicle group, 4/12 in the HI group treated with sildenafil 2 mg/kg, 2/11 in the HI group treated with sildenafil 10 mg/kg, and 3/11 in the HI group treated with sildenafil 50 mg/kg; no animals died in the sham groups.

Sildenafil Improved Neurological Deficits in the HI Animals

HI induced impairment of several parameters in the gait analysis. Treatment with sildenafil, even in small doses, led to an improvement of the neurological deficits as measured by the gait analysis (FIG. 1). The size of the print area (FIG. 1a), the size of maximum contact area (FIG. 1b), the size of the print length (FIG. 1c), the duration of the initial dual stance (FIG. 1d) and the terminal dual stance (FIG. 1e) were different between the groups. Some of these parameters—including the print length—even showed an increase with the high-dose of sildenafil. The maximum intensity, the base of support, the stride length, the step sequence regularity index, the swing duration, and the cadence were not different between the HI animals treated with vehicle and the sham vehicle rat pups.

The sham animals treated with the different doses of sildenafil had similar gait parameters compared to the sham vehicle rat pups.

Sildenafil, Especially at Higher Doses, Improved Brain Injury Recovery in the HI Animals at P30

Figure 2A:
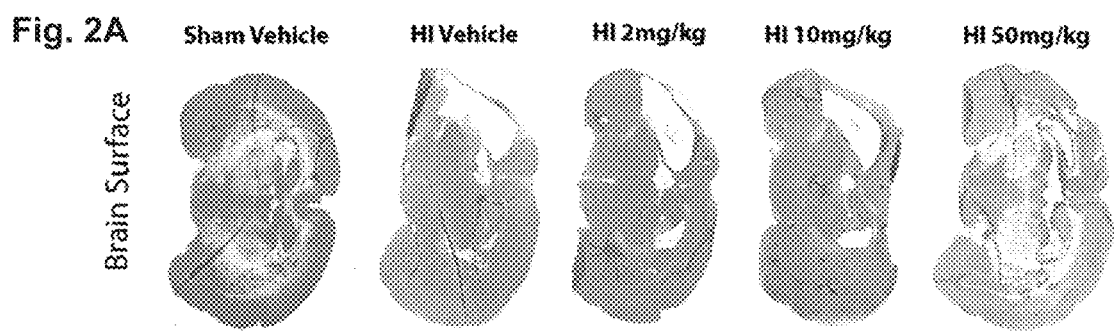
FIGS. 2A to 2C illustrate hematoxylin and eosin-stained coronal brain results in HI and sham rat pups treated with sildenafil or vehicle. (A) Representative hematoxylin and eosin-stained coronal brain sections at the level of the hippocampus. (B) Left/right hemisphere surface ratio (median with Interquartile Range, IQR). (C) Total brain size (median with IQR). The result identified with *,  and * correspond to *p<0.05, p<0.01, *p<0.001, significant for comparisons vs. sham vehicle rat pups. Kruskal-Wallis test with Dunn's post hoc comparison tests.

HI caused a significant reduction in the size of the left hemisphere (i.e., ipsilateral to the carotid ligation) compared to the right hemisphere (i.e., controlateral to the carotid ligation) as well as the total brain size at P30. Treatment with sildenafil led to an improvement in the size of the left hemisphere as well as total brain size; the effect was more pronounced with the high dose of sildenafil (FIG. 2a).

Figure 2B:
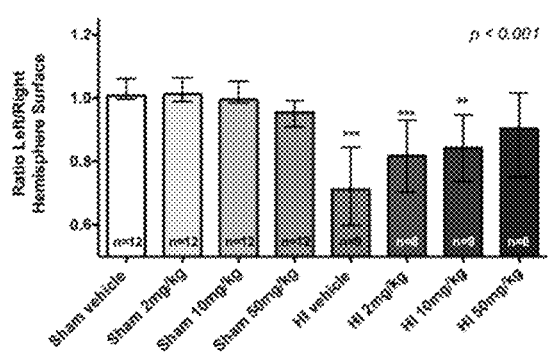
Figure 2C:
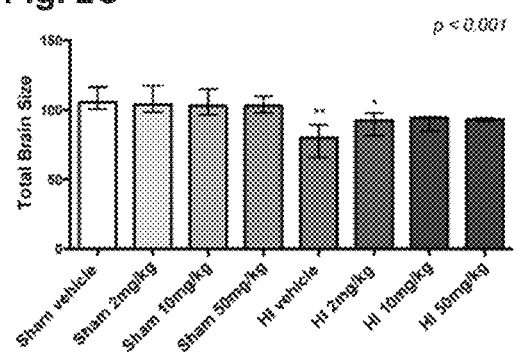

Ratios between the left and right hemisphere surfaces were significantly reduced in the HI animals treated with vehicle [median (interquartile ranges): 0.71 (0.59; 0.84), p<0.001)], compared to the sham vehicle rat pups [1.00 (0.99; 1.06)] (FIG. 2b). Total brain size was also significantly reduced in the HI animals treated with vehicle [80 (65.82; 89.32), p<0.01], compared with the same vehicle rat pups [105.5 (100.7; 116.4)] (FIG. 2c). Treatment with the low-dose and the medium-dose of sildenafil improved brain injury recovery, but the ratios between left and right hemispheres remained different compared to the sham vehicle rat pups, respectively 0.81 (0.70; 0.93) in the HI group treated with sildenafil 2 mg/kg (p<0.001), and 0.84 (0.73; 0.94) in the HI group treated with sildenafil 10 mg/kg (p<0.01). Similarly, total brain size was improved in the low-dose of sildenafil, but remained different compared to sham vehicle rat pups [92.19 (81.51; 97.58), p<0.05]. Treatment with the high-dose of sildenafil improved brain injury recovery to the level that the left-to-right hemisphere ratio was no longer statistically different between the HI animals treated with 50 mg/kg of sildenafil [0.90 (0.75; 1.01)] and the sham vehicle rat pups (FIG. 2b). Total brain size was no longer significantly different after treatment with the medium-dose [94.05 (84.4; 95.0)] and the high-dose of sildenafil [93.05 (91.53; 93.95)] compared to sham vehicle rat pups (FIG. 2c).

The sham animals treated with the different doses of sildenafil had similar ratios between the left and right hemispheres and had similar total brain size, compared to the sham vehicle rat pups (FIG. 2b and FIG. 2c).

Sildenafil Leads to an Increase in Neuronal Number Near the Infarct Boundary Zone in the Cortex at P30

HI did not cause a significant increase in the neuronal number near the infarct boundary zone of the cortex at P30. Treatment with sildenafil led to a significant increase in the neuronal number in the same injured area. Again, this effect was more pronounced with the high dose of sildenafil.

The number of NeuN positive mature neurons was similar near the infarct boundary zone in the HI animals treated with vehicle [852 (662; 940) neurons/mm$^2$], compared to the corresponding zone of the sham vehicle rat pups [696 (523; 811) neurons/mm$^2$] (FIG. 3a, FIG. 3b). HI also did not have a significant effect on the neuronal number [765 (592; 820) neurons/mm$^2$] in the corresponding region of the contralateral (i.e., right) cortex, compared to the sham vehicle rat pups [740 (595; 812) neurons/mm$^2$] (FIG. 3c). Treatment with low-dose (2 mg/kg) of sildenafil significantly increased the neuronal number to 1118 (1069; 1238) neurons/mm$^2$ (p<0.01), compared to the sham vehicle rat pups. With the medium-dose (10 mg/kg) of sildenafil, the neuronal number further increased to 1222 (1170; 1338) neurons/mm$^2$ (p<0.001). Treatment with the high-dose of sildenafil led to the highest increase in cortical neuronal number [1368 (1292; 1444) neurons/mm$^2$, p<0.001] (FIG. 3a, FIG. 3b). In the corresponding region of the contralateral cortex, treatment with the medium-dose and the high-dose of sildenafil also led to an increase in neuronal number [respectively, 999 (930; 1107) neurons/mm$^2$, p<0.001, and 1019 (948; 1106) neurons/mm$^2$, p<0.001]; treatment with the low-dose of sildenafil did not significantly increase neuronal number in same region of the controlateral cortex [808 (586; 963) neurons/mm$^2$] (FIG. 3c).

Sildenafil did not have a Significant Effect on the Endothelial Cells Number and on Microvessel Density at P30

HI did not have a significant effect on the endothelial cells number [211 (144; 277) endothelial cells/mm$^2$], compared to the sham vehicle rat pups [247 (210; 256) endothelial cells/mm$^2$] (FIG. 4b). Furthermore, HI did not have a significant effect on microvessel density [256 (218; 266) microvessels/mm$^2$], compared to the sham vehicle rat pups [267 (250; 278) microvessels/mm$^2$] (FIG. 4a, FIG. 4c).

Also, no significant changes occurred in the endothelial cells numbers in the HI animals treated with a low-dose, medium-dose, and high-dose of sildenafil, compared to the sham vehicle rat pups: respectively 230 (158; 273) endothelial cells/mm$^2$ in the HI group treated with sildenafil 2 mg/kg, 196 (157; 225) endothelial cells/mm$^2$ in the HI group treated with sildenafil 10 mg/kg, and 193 (151; 217) endothelial cells/mm$^2$ in the HI group treated with sildenafil 10 mg/kg (FIG. 4b). Similarly, no significant changes occurred in microvessel density in the HI animals treated with a low-dose and medium-dose of sildenafil, compared to the sham vehicle rat pups: respectively 257, 222-277 microvessels/mm$^2$ in the HI group treated with sildenafil 2 mg/kg (p>0.05), and 246, 221-263 microvessels/mm$^2$ in the HI group treated with sildenafil 10 mg/kg (p>0.05). Only the high-dose (50 mg/kg) of sildenafil significantly decreased the microvessel density near the infarct boundary zone [211 (182; 221), p<0.01], compared to the sham vehicle rat pups (FIG. 4c).

As shown in this example, sildenafil—especially at higher doses, administered orally during 7 consecutive days following neonatal hypoxic-ischemia at term-equivalent age (P10)—can improve neurological deficits assessed by gait analysis at P27, and can also improve cortical recovery and increase the neuronal number near the infarct boundary zone in the cortex at P30. This demonstrates the longer-term effect of different doses of sildenafil in a rat model of term neonatal hypoxic-ischemic encephalopathy.

Without willing to be bound to theory, the improved cortical recovery in the HI animals treated with sildenafil can be associated with a significant increase in the number of neurons near the infarct boundary zone of the cortex at P30, but also in the contralateral cortex with the high doses of sildenafil. This increase in neuronal number was minimal near the infarct boundary zone in the HI animals treated with vehicle alone.

In the present example, sildenafil treatment did not have a significant effect on the number of endothelial cells in the cortical regions adjacent to the infarct boundary in the HI rat pups at P30. Two different stainings for the endothelial cells, such as lectin labels blood vessels as well as microglia were used. However, microglia have a distinct morphology from vessels, which permits their exclusion from the endothelial cell count when using lectin. Similar results were found when using collagen IV stainings with the exception of a small decrease in microvessels density with the high-dose of sildenafil. Thus, without willing to be bound to theory, the neurorestorative effect of sildenafil in the rat model of term neonatal hypoxia-ischemia may be independent of the neovascularization in the cortical regions adjacent to the infarct boundary at P30.

Treatment with sildenafil, even at the lower-dose, can improve the gait parameters in the rat pups. It has also been shown that sildenafil does not impact normal brain growth. Indeed, the sham animals treated with the different doses of sildenafil did not have any differences in brain size. The results for the HI animals suggest that sildenafil can enhance the brain repair processes, with a substantial improvement of functional and structural recovery.

The present example protocol has been chosen to reproduce as much as possible what would be feasible for human term asphyxiated newborns. Sildenafil was administrated by oral route instead of the more traditional intraperitoneal or subcutaneous route, since oral sildenafil is a commonly used route with human newborns. In addition it is known that oral sildenafil displays a good oral bioavailability.

Furthermore, sildenafil administration started 12 hours after the hypoxic-ischemic event, and not immediately after, which took into consideration the delay that it would take to identify those human newborns at risk of brain injury, despite hypothermia treatment. Finally, the treatment was 7 days after the initial event to potentially continue acting on the cascades of chemical reactions triggered following hypoxia-ischemia.

The fact that sildenafil had a beneficial effect, even when only started 12 hours after the HI insult, highlights the probable neurorestorative role of sildenafil treatment in the brain. Therefore, sildenafil may be used for the treatment of brain injury following hypoxia-ischemia at term-equivalent age.

As an additional remark, it is reported that both sham rat pups and HI rat pups received the same sedation, permitting to control for the effect of sedation.

Use of sildenafil after term neonatal hypoxia-ischemia to increase mature oligodendrocytes in the white matter and to improve myelination in rats.

The effect of sildenafil on the presence of neuroinflammation and consequent impairments in myelination after neonatal hypoxia-ischemia (HI) at term-equivalent age was investigated.

Neonatal HI was induced in male Long-Evans rat pups at postnatal day 10 (P10) by left common carotid ligation followed by 2-hour exposure to 8% oxygen. Sham operated rat pups served as control. Both groups were administered 0 (vehicle), 2, 10 or 50 mg/kg of sildenafil twice daily by oral gavage, starting from 12 hours post-HI for 7 consecutive days. At P30, rats were sacrificed and their brains extracted. Hematoxylin and eosin staining was performed to analyze the structure of the myelin sheath. Olig2 and CC-1 immunostaining were performed to assess the proportion of mature oligodendrocyte to total oligodendrocytes. GFAP, Iba1, and Mac2 immunostaining was used to label reactive astrocytes and activated microglia. Collagen IV was used to investigate microvessels. Corpus callosum and left external capsule were the 2 regions where these markers were assessed to evaluate "white matter".

HI caused a significant decrease in myelin sheath thickness in the corpus callosum and left external capsule compared to sham vehicle rats. Sildenafil (all dosage) reverted the myelin sheath thickness back to levels comparable to sham vehicle rat animals. Hypoxic-ischemia was not associated with a significant difference in the number of total oligodendrocytes or mature oligodendrocytes in the corpus callosum or left external capsule, compared to the sham group.

High doses of sildenafil (50 mg/kg) significantly increased the number of total oligodendrocytes as well as mature oligodendrocytes in the corpus callosum. There were no changes in number of total and mature oligodendrocytes in the left external capsule after sildenafil. There was a significant reduction in reactive astrocytosis and microgliosis in the corpus callosum and left external capsule with higher doses of sildenafil. There were no changes in microvessel density in the white matter.

Therefore, oral sildenafil, especially at higher dosage, may reduce neuroinflammation and increase oligodendrogenesis following neonatal hypoxic-ischemia. This can be one of the involved mechanisms through which sildenafil administrated following term neonatal hypoxiaischemia decreases brain injury by improving myelination and thus the structural integrity of white matter.

Use of Sildenafil for Treating Injury of the Cerebellum Following Hypoxia-Ischemia at Term-Equivalent Age The effect of sildenafil on the injury of the cerebellum following hypoxia-ischemia at term-equivalent age was investigated.

Neonatal HI was induced in male Long-Evans rat pups at postnatal day 10 (P10) by left common carotid ligation followed by a 2-hour exposure to 8% oxygen; sham operated rat pups served as the control. Both groups were randomized to oral sildenafil (2, 10, or 50 mg/kg) or vehicle twice daily for 7 consecutive days. At P30, the rats were sacrificed, and the cerebellum was extracted. The internal granular layers and molecular layers of the cerebellum were measured across all groups on cresyl violet-stained cerebellum sections. Astrocytes expressing Vascular Endothelial Growth Factor (VEGF) in the internal granular layers and molecular layers were quantified using immunohistochemistry.

There was a significant decrease ($p<0.05$) in the thickness of the internal granular layers and molecular layers in both the anterior (lobules 3 and 4) and posterior (lobules 8 and 9) cerebellum of rat pups exposed to hypoxia-ischemia. There was a significant increase in VEGF expressing astrocytes in the internal granular layers of the anterior cerebellar sections in the same animals. Treatment with sildenafil led to an improvement in the overall thickness of these layers and reduction of VEGF expressing astrocytes. A positive correlation was found between the surface area of the ipsilateral (injured) hemisphere of the cerebrum and the size of the granular layer of the cerebellum. There was also a positive correlation between the surface area of the ipsilateral (injured) hippocampus in the cerebrum and the size of the molecular layer of the cerebellum.

Therefore, the cerebellum seems susceptible to injury following hypoxia-ischemia at term equivalent age and sildenafil may improve the injury to the cerebellum, like in the cerebrum.

Use of Sildenafil to Repair Hippocampal Brain Injuries in Term Neonatal Encephalopathy The effect of sildenafil on hippocampal brain injury activation of neuroinflammation after neonatal hypoxia-ischemia (HI) at term-equivalent age was investigated.

Neonatal HI was induced in male Long-Evans rat pups at postnatal day 10 (P10) by left common carotid ligation followed by 2-hour exposure to 8% oxygen. Sham operated rat pups served as control. Both groups were administered 0 (vehicle), 2, 10 or 50 mg/kg of sildenafil twice daily by oral gavage, starting from 12 hours post-HI for 7 consecutive days. At P30, rats were sacrificed and their brains extracted. CA1, CA3 and dentate gyrus (DG) areas of the ipsilateral hippocampus were analyzed for microgliosis (Iba1) and astrogliosis (GFAP), neuronal number (NeuN), and vascular density (collagen IV).

HI caused a significant increase in the number of microglia and astrocytes in CA1, CA3 and DG regions of the hippocampus, compared to sham vehicle rat animals. There were no significant changes in neuronal number or vascular density in the hippocampus of HI vs sham animals. Higher doses of Sildenafil (10 mg/kg and 50 mg/kg) significantly reduced the number of activated microglia and reactive astrocytes in CA1 and dentate gyrus of the hippocampus in HI animals. The highest dose of Sildenafil (50 mg/kg) significantly increases neuronal number in the dentate gyrus of HI animals compared to sham vehicle animals. There were no changes in vascular density between the treatment groups and the control group.

Therefore, oral sildenafil, especially at higher dosage, may reduce neuroinflammation following neonatal hypoxic-ischemia and increases neuronal number in the hippocampus.

Example 2: Use of Sildenafil to Improves Functional and Structural Outcome of Retinal Injury Following Term Neonatal Hypoxia-Ischemia 2.1 Animals All experiments were conducted in accordance with the Association for Research in Vision and Ophthalmology Statement for the use of animals in ophthalmic and vision research, and were approved by the local animal care committee. Adult female Long-Evans rats with their male-only litters (Harlan Laboratories) were received, housed under standard environment, and allowed food and water ad libitum. Rat pups remained with their mother until weaning at postnatal day 21 (P21).

2.2 Induction of Term Neonatal Hypoxic-Ischemic Encephalopathy (HIE)

A well-established rat model of term neonatal HIE (Vannucci model) (Patel S D et al., 2014, Patel S D et al., 2015; Recker R et al., 2009; Rice J E, $3^{rd}$ et al., 1981) combining a left common carotid artery ligation and a 2-hour exposure to 8% oxygen, was used with 10-day-old rat pups as previously described (Jung S et al., 2015) since this model mimics the patterns of brain injury observed in human term asphyxiated newborns (Patel S D et al., 2014, Patel S D et al., 2015; Recker R et al., 2009; Rice J E, $3^{rd}$ et al., 1981) and produces concomitant retinal injury (Jung S et al., 2015). Rats undergoing both the ligation and hypoxia were considered the HI group. Sham operated rats (identical procedure as the HI group, but without ligation and hypoxia) served as the control group.

2.3 Sildenafil Administration

HI and sham rat pups were weighed daily and then randomized to sildenafil (Viagra®; Pfizer Canada Inc., Kirkland, QC, Canada) or vehicle (Ora-Blend® suspension media; Perrigo Company PLC, Minneapolis, Minn., USA) twice daily by oral gavage, starting from 12 hours post-HI for 7 consecutive days. Different doses of sildenafil—i.e., low (2 mg/kg), medium (10 mg/kg), and high (50 mg/kg)—were used in the HI and sham rat pups (n=4-7 animals/group).

2.4 Retinal Function

At P29, full-field flash electroretinograms (ERGs) (LKC Technologies, Inc., Gaithersburg, Md., USA) were recorded binocularly following a previously described protocol (Jung S et al., 2015). The maximum mixed rod-cone a-wave amplitude (Hood D C et al., 1990) was measured from the pre-stimulus baseline to the trough of the a-wave, and the maximum mixed rod-cone b-wave amplitude (Miller et al., 1970; Stockton R A et al., 1989) was measured from the trough of the a-wave to the peak of the b-wave. The photopic b-wave amplitude was measured from the baseline to the b-wave peak, and the photopic negative response (PhNR) (Li B et al., 2015; Machida S et al., 2008) was measured from the baseline to the most negative trough following the photopic b-wave. Measurements were performed using EM for Windows® software (LKC Technologies, Inc., Gaithersburg, Md., USA). When the peak of the b-wave could not be determined, the amplitude of the b-wave was measured at the time when the b-wave peaked in the control animals.

2.5 Retinal Structure

At P30, the animals were sacrificed, and the eyes were enucleated. Retinal histology was performed as per a previously described protocol (Jung S et al., 2015). Using AxioVision® software (Version 4.8.2.0; Carl Zeiss Microscopy GmbH, Jena, Germany), the thicknesses of the different retinal layers were measured at approximately 1000 μm inferior from the optic nerve head, a region that showed the most prominent HI-induced damage (Jung S et al., 2015). For retinal reconstruction, retinal segments of 75 μm in width—taken at every 340 μm along the entire length of the superior and inferior retinas—were assembled side by side (Adobe Photoshop®, Adobe Systems Inc. San Jose, Calif., USA) to yield a pan-retinal view. Then, the retinal layer thickness was plotted against eccentricity to obtain the spider graphs (FIG. 7B).

2.6 Statistical Analysis

The HI and sham rat pups were subdivided into the following groups: vehicle (0 mg/kg) or sildenafil 2 mg/kg, 10 mg/kg, or 50 mg/kg. Differences in the ERG amplitudes and retinal thicknesses between the different doses of sildenafil and the vehicle group were assessed with the respective effect sizes (non-standardized difference of the means) and corresponding 95% confidence intervals.

2.7 Results

Sildenafil Improved the Retinal Function Outcome in the HI Rat Pups at P29

HI caused impairment in the retinal function of the left eye (i.e., ipsilateral to the carotid ligation) of the rat pups treated with vehicle alone. HI induced an attenuation in the amplitude of the ERG mixed rod-cone b-wave, photopic b-wave, and PhNR, and to a lesser extent, of the mixed rod-cone a-wave, compared to the sham vehicle rat pups (Table 1 and FIG. 5). HI did not affect the ERGs recorded from the right eyes (i.e., contralateral to the carotid ligation).

The left eyes of the HI animals showed a dose-dependent improvement in all ERG parameters with treatment with different doses of sildenafil, where higher doses were associated with greater effect sizes (Table 1 and FIG. 5). The 50 mg/kg dose of sildenafil induced significantly improved response in terms of all ERG parameters, whereas the 10 mg/kg of sildenafil induced significantly improved response in terms of the mixed rod-cone b-wave, the photopic b-wave, and the PhNR, but not the a-wave.

Interestingly, sildenafil had no significant effect on the ERG amplitudes of the right eyes of the HI rat pups (i.e., contralateral to the carotid ligation) and both eyes of the sham rat pups treated with the different doses of sildenafil.

TABLE 1

| | Electroretinogram amplitudes. | | | | | | | |
|---|---|---|---|---|---|---|---|---|
| | Sham - Veh (n = 7) | Sham - Sild 2 mg/kg (n = 5) | Sham - Sild 10 mg/kg (n = 7) | Sham - Sild 50 mg/kg (n = 6) | HI - Veh (n = 6) | HI - Sild 2 mg/kg (n = 5) | HI - Sild 10 mg/kg (n = 6) | HI - Sild 50 mg/kg (n = 4) |
| | | | | OS | | | | |
| Mixed rod-cone a-wave, μV | 395.97 ± 44.90 | 356.22 ± 25.73 | 302.64 ± 19.39 | 383.13 ± 33.82 | 216.28 ± 25.99 | 283.38 ± 27.62 | 288.92 ± 43.38 | 349.73 ± 27.14 |

TABLE 1-continued

Electroretinogram amplitudes.

|  | Sham - Veh (n = 7) | Sham - Sild 2 mg/kg (n = 5) | Sham - Sild 10 mg/kg (n = 7) | Sham - Sild 50 mg/kg (n = 6) | HI - Veh (n = 6) | HI - Sild 2 mg/kg (n = 5) | HI - Sild 10 mg/kg (n = 6) | HI - Sild 50 mg/kg (n = 4) |
|---|---|---|---|---|---|---|---|---|
| Effect size (95% CI) |  | −39.75 (−168.85, 89.34) | −93.33 (−199.89, 13.24) | −12.84 (−140.19, 114.52) |  | 67.10 (−18.95, 153.14) | 72.63 (−40.04, 185.31) | 133.44 (43.66, 223.22) |
| Mixed rod-cone b-wave, μV | 870.51 ± 96.79 | 755.50 ± 60.68 | 714.80 ± 65.07 | 860.93 ± 62.52 | 135.18 ± 32.67 | 138.68 ± 20.89 | 548.88 ± 132.35 | 628.83 ± 124.89 |
| Effect size (95% CI) |  | −115.01 (−396.99, 166.96) | −155.71 (−409.83, 98.40) | −9.58 (−273.44, 254.28) |  | 3.50 (−88.67, 95.66) | 413.70 (109.95, 717.45) | 493.64 (247.26, 740.02) |
| Photopic b-wave, μV | 250.69 ± 21.51 | 209.54 ± 2.67 | 252.53 ± 25.47 | 235.05 ± 14.33 | 10.38 ± 5.90 | 20.26 ± 6.46 | 167.90 ± 41.53 | 182.38 ± 42.41 |
| Effect size (95% CI) |  | −41.15 (−98.86, 16.57) | 1.84 (−70.80, 74.48) | −15.64 (76.69, 43.42) |  | 9.88 (−9.93, 29.68) | 157.52 (64.05, 250.98) | 171.99 (92.83, 251.15) |
| PhNR, μV |  | 100.89 ± 9.00 | 91.36 ± 5.42 | 98.24 ± 11.07 | 96.83 ± 6.21 | 18.45 ± 3.36 | 26.04 ± 15.07 | 73.78 ± 18.57 | 89.03 ± 22.35 |
| Effect size (95% CI) |  | −9.53 (−35.57, 16.52) | −2.64 (−33.72, 28.43) | −4.05 (−28.97, 20.87) |  | 7.56 (−24.32, 39.50) | 55.33 (13.29, 97.38) | 70.58 (28.70, 112.45) |
| OD |  |  |  |  |  |  |  |  |
| Mixed rod-cone a-wave, μV | 400.29 ± 28.35 | 454.30 ± 14.54 | 329.26 ± 26.30 | 398.62 ± 26.75 | 429.20 ± 53.69 | 468.34 ± 36.85 | 351.50 ± 25.93 | 383.08 ± 36.96 |
| Mixed rod-cone b-wave, μV | 829.76 ± 63.30 | 946.16 ± 38.24 | 735.33 ± 61.79 | 896.70 ± 24.97 | 955.78 ± 79.43 | 1017.4 ± 78.19 | 788.42 ± 58.46 | 815.50 ± 88.48 |
| Photopic b-wave, μV | 254.49 ± 23.01 | 254.36 ± 27.18 | 267.71 ± 15.35 | 268.82 ± 17.95 | 302.07 ± 27.54 | 302.76 ± 32.30 | 257.62 ± 24.06 | 284.73 ± 11.08 |
| PhNR, μV | 109.44 ± 5.01 | 110.62 ± 3.98 | 105.24 ± 7.06 | 119.45 ± 9.32 | 125.83 ± 11.70 | 129.36 ± 15.27 | 110.98 ± 12.24 | 126.93 ± 8.49 |

Abbreviations: CI, confidence interval of the effect size; OS, ipsilateral left eye; OD, contralateral right eye; PhNR, photopic negative response; sild, sildenafil; veh, vehicle.
Effect size: calculated compared to the vehicle rat pups.

Sildenafil Improved the Retinal Structure Outcome in the HI Animals at P30

Considering the ERG results, retinal histology was performed only on the left eyes of the sham vehicle group and the HI groups treated with the different doses of sildenafil.

HI induced damages to the retinal structure in the left eyes (i.e., ipsilateral to the carotid ligation) of the rat pups treated with vehicle (FIGS. 6A and 6B). The total retinal thickness was reduced in the HI vehicle rat pups, compared to the sham vehicle rat pups (Table 2 and FIGS. 6A and 6B). Specifically, the HI vehicle rat pups showed a thinning of the inner retinal layers [i.e., inner nuclear layer (INL), inner plexiform layer, and retinal ganglion cell/fiber layer (RGC/FL] and the outer plexiform layer (OPL), compared to the sham vehicle rat pups. In contrast, the thickness of the outer nuclear layer (ONL) was greater in the HI rat pups treated with the vehicle compared to the sham vehicle rat pups. No significant difference was found in the thickness of the retinal pigment epithelium (RPE), the outer segment (OS), and the inner segment (IS) between groups.

The thicknesses of the affected layers (total retina, ONL, OPL, INL, IPL, RGC/FL) in the HI animals showed a dose-dependent improvement with treatment with different doses of sildenafil. Again, higher doses were associated with greater effect sizes (Table 2 and FIGS. 6A and 6B). The 10 mg/kg and the 50 mg/kg doses induced significantly improved response in terms of thicknesses of all the affected layers.

TABLE 2

Thicknesses of the retinal layers.

|  | Sham - Veh | HI - Veh | HI - Sild 2 mg/kg | HI - Sild 10 mg/kg | HI - Sild 50 mg/kg |
|---|---|---|---|---|---|
| Total thickness, μm | 244.14 ± 16.56 | 152.55 ± 10.48 | 167.28 ± 2.63 | 205.64 ± 14.20 | 205.80 ± 14.22 |
| Effect size (95% CI) |  |  | 14.72 (−11.71, 41.16) | 53.09 (9.24, 96.94) | 53.25 (10.02, 96.47) |
| RPE thickness, μm | 8.38 ± 0.32 | 8.62 ± 0.23 | 8.88 ± 0.24 | 7.89 ± 0.35 | 8.03 ± 0.27 |
| Effect size (95% CI) |  |  | 0.25 (−0.51, 1.02) | −0.73 (−1.69, 0.24) | −0.59 (−1.43, 0.25) |
| OS thickness, μm | 32.45 ± 4.70 | 37.74 ± 7.28 | 38.14 ± 3.66 | 29.18 ± 2.14 | 27.87 ± 2.09 |
| Effect size (95% CI) |  |  | 0.40 (−19.53, 20.33) | −8.55 (−24.72, 7.62) | −9.86 (−28.39, 8.66) |
| IS thickness, μm | 16.50 ± 1.04 | 21.67 ± 3.61 | 23.83 ± 3.12 | 14.43 ± 1.15 | 14.16 ± 0.25 |

TABLE 2-continued

Thicknesses of the retinal layers.

| | Sham - Veh | HI - Veh | HI - Sild 2 mg/kg | HI - Sild 10 mg/kg | HI - Sild 50 mg/kg |
|---|---|---|---|---|---|
| Effect size (95% CI) | | | 2.16 (−9.52, 13.84) | −7.24 (−15.35, 0.88) | −7.50 (−16.37, 1.36) |
| ONL thickness, μm | 57.08 ± 4.02 | 70.17 ± 4.01 | 70.88 ± 2.88 | 50.95 ± 0.76 | 52.81 ± 1.06 |
| Effect size (95% CI) | | | 0.71 (−11.36, 12.79) | −19.22 (−27.79, −10.64) | −17.36 (−27.51, −7.21) |
| OPL thickness, μm | 10.55 ± 0.52 | 0.81 ± 0.81 | 5.72 ± 3.05 | 9.48 ± 0.38 | 9.76 ± 0.84 |
| Effect size (95% CI) | | | 4.91 (−2.81, 12.63) | 8.67 (6.70, 10.63) | 8.95 (6.11, 11.79) |
| INL thickness, μm | 37.03 ± 3.02 | 9.76 ± 0.83 | 14.71 ± 2.57 | 29.50 ± 1.70 | 31.42 ± 1.66 |
| Effect size (95% CI) | | | 4.94 (−1.68; 11.57) | 19.74 (14.85; 24.62) | 21.65 (17.11; 26.19) |
| IPL thickness, μm | 59.79 ± 3.08 | 2.85 ± 2.31 | 2.95 ± 2.60 | 44.93 ± 7.35 | 44.25 ± 11.86 |
| Effect size (95% CI) | | | 0.11 (−8.40, 8.61) | 42.08 (21.79, 62.37) | 41.40 (11.85, 70.96) |
| RGC/FL thickness, μm | 22.37 ± 1.09 | 0.91 ± 0.91 | 2.28 ± 2.28 | 19.28 ± 3.36 | 17.50 ± 4.07 |
| Effect size (95% CI) | | | 1.37 (−4.63, 7.37) | 18.37 (9.16, 27.58) | 16.59 (6.38, 26.80) |

Abbreviations: RPE, retinal pigment epithelium; CI, confidence interval of the effect size; OS, outer segment; IS, inner segment; ONL, outer nuclear layer; OPL, outer plexiform layer; INL, inner nuclear layer; IPL, inner plexiform layer; RGC/FL, retinal ganglion cell/fiber layer; sild, sildenafil; veh, vehicle.
Effect size: calculated compared to the HI vehicle rat pups.

The pattern of retinal injury was not uniform along the superior-inferior axis of the retina (FIG. 7A). The spider graph revealed that the HI rat pups treated with vehicle had thinner INL, IPL, and RGC/FL, which spanned almost all retinal eccentricity, while the increase in ONL and the decrease in OPL thicknesses were detected mostly in the central retina (FIG. 7B). Treatment with the low-dose of sildenafil did not seem to reverse any of the HI-induced changes in retinal thickness, except in the inferior retina, where the areas showing a thinning of the OPL were limited to a smaller portion of the central region, compared to the HI rat pups treated with the vehicle. In contrast, the HI rat pups treated with the medium and high doses of sildenafil disclosed a nearly normal inner retina at almost all retinal eccentricities along the superior-inferior axis.

Neonatal HI induces significant retinal damage, including a reduction in the ERG amplitudes and a thinning of the retina. HI affects mostly the inner retina, both functionally (i.e., attenuation of the ERG b-wave and PhNR) and structurally (i.e., destruction of the INL, IPL, and RGC/FL). The photoreceptor function (attenuation of the ERG a-wave) is also affected, but to a lesser extent.

It has been shown that treatment with the different doses of sildenafil can lead to a dose-dependent improvement in the ERG amplitudes and in the retinal layer thicknesses, with higher doses associated with greater effect sizes. The 50 mg/kg dose of sildenafil induced an improved response in terms of all ERG parameters, whereas the 10 mg/kg of sildenafil induced an improved response in terms of the mixed rod-cone b-wave, the photopic b-wave, and the PhNR, but not the a-wave. The 10 mg/kg and the 50 mg/kg doses induced an improved response in terms of thicknesses of all the affected layers. This study demonstrates the therapeutic role of sildenafil on retinal injury induced by neonatal HI at term-equivalent age.

Without willing to be bound to theory, a possible mechanism can be through a vascular effect. The endothelial cells and the smooth muscles of the retinal vasculature, the choroidal vasculature, and the ophthalmic artery express PDE5. It is known that sildenafil increases the diameter of some of these blood vessels and consequently increases the ocular blood flow (in porcine eyes as well as in healthy human subjects). Thus, in the short-term, sildenafil may help restore the blood flow to the affected retina.

In the present example, sildenafil was administered with a 12-hour delay and continued for 7 days; thus, a process other than acute vasodilation may be involved. Another possible vascular effect of sildenafil may be through the modulation of retinal angiogenesis. It has been shown that sildenafil administration in a neonatal mouse model of oxygen-induced retinopathy can prevent the hyperoxia-induced retinal vaso-obliteration through HIF-α stabilization, which in turn prevented the retinal neovascularization known to take place when the pups are returned to normoxia.

The beneficial effects of sildenafil may also arise from non-vascular mechanisms. Sildenafil has been shown to upregulate neurotrophic factors in adult rodent models of neurological diseases, reduce neuroinflammation, and activate pro-survival signalling pathways, which have resulted in reduced neuronal loss and synaptic damage, and enhanced neurogenesis. In a premature rat model of brain injury, sildenafil has been shown to decrease neuronal apoptosis and microglial activation. Since neuronal apoptosis has been shown to peak at 24 hours post-HI in the neonatal retina, the Sildenafil administered 12 hours post-HI may have limited apoptosis and further degeneration by its possible anti-apoptotic and anti-inflammatory effects.

Interestingly, the outer segment of photoreceptors expresses PDE6, which is known to be involved in photoreceptor survival and phototransduction. In addition, selective inhibition of PDE6 has been shown to increase intracellular cGMP in the photoreceptors and lead to photoreceptor degeneration. Sildenafil also inhibits PDE6, but with a reduced efficiency. In the present example, sildenafil did not induce photoreceptor degeneration. In fact, treatment with sildenafil restored the function of the photoreceptors, which had been impaired following hypoxia-ischemia at term-equivalent age.

It has been shown that sildenafil does not affect normal retinal function, as demonstrated by the absence of a difference in the ERG amplitudes between the sham rat pups treated with different doses of sildenafil and the sham vehicle rat pups. It has also been shown that sildenafil can limit or repair the retinal injury resulting from neonatal hypoxia-ischemia, with a substantial improvement of retinal function and structure compared to the untreated rat pups.

The present example protocol has been chosen to reproduce as much as possible what would be feasible for human term asphyxiated newborns. Sildenafil was administered by oral route instead of the more traditional intraperitoneal or subcutaneous route, since oral sildenafil is the most commonly used route with human newborns. It is known that oral sildenafil displays a good oral bioavailability. It is believed that oral sildenafil reaches the retina, since it is known to transiently affect the ERG in healthy human subjects 1 hour after intake.

Dosages in the present example were chosen so that they correspond somewhat to the equivalent recommended amount for human newborns ranging from low doses that are usually initially used to maximal described doses. In addition, sildenafil administration was started 12 hours after the hypoxic-ischemic event, taking into consideration the delay that it would take to identify human newborns at risk of developing injury despite the hypothermia treatment. Finally, the treatment was repeated for 7 days so that it would potentially continue acting on the cascades of chemical reactions triggered following hypoxia-ischemia.

The fact that sildenafil had a beneficial effect even when started 12 hours after the HI insult highlights the probable neurorestorative role of sildenafil in the retina, with a wider treatment window compared to neuroprotective strategies. The present results suggest that sildenafil may be used for the treatment of retinal injury following HI at term-equivalent age.

In conclusion, treatment with oral sildenafil provided a dose-dependent beneficial effect on the function and structure of the retina in a rat model of term neonatal encephalopathy. In addition, treatment with sildenafil had no adverse effect on normal retinal function. These results highlight the potential therapeutic role of sildenafil for retinal injury induced by neonatal hypoxia-ischemia at term-equivalent age.

Use of Sildenafil to Modulate Retinal Inflammation Following Term Neonatal Hypoxic-Ischemic Injury The effect of sildenafil on improvement of retinal injuries following term neonatal asphyxia was investigated.

Neonatal hypoxia-ischemia (HI) was induced in male Long-Evans rat pups at postnatal day 10 (P10) by left common carotid ligation followed by 2-hour exposure to 8% oxygen. 12 hours following HI, animals were randomly administered 0 (vehicle), 2, 10 or 50 mg/kg of sildenafil for 7 consecutive days. At P30, rats were sacrificed and their eyes were extracted. Immunohistochemistry was performed to examine retinal ganglion cells (Brn3a), bipolar cells (Chx10), astrocytes (GFAP) and microglia (Iba1) in order to assess the neuronal count and the inflammatory response in the retina following HI and the impact of the sildenafil treatment.

In the retina, HI caused a decrease in the number of retinal ganglion cells and bipolar cells, as well as an increase in inflammation marked by an increase in the number of astrocytes. Sildenafil treatment restored the number of retinal ganglion cells and bipolar cells. Furthermore, the treatment reduced neuroinflammation by decreasing the number of astrocytes. Therefore, sildenafil can prevent neuronal death and modulate inflammation.

Example 3: Use of Sildenafil to Repair Retinopathy of Prematurity after Exposure to Hyperoxia The therapeutic effect of sildenafil on retinal function and structure in a rat model of ROP was investigated.

3.1 Method

Sprague-Dawley rats were exposed to hyperoxia (i.e., 80% oxygen) interrupted by three 0.5-hour periods of normoxia (i.e., 21% oxygen) per day or room air only (i.e., 21% oxygen) from post-natal day 4 (P4) to 14 (P14). Pups were then housed in room air. Sildenafil (50 mg/kg) or vehicle was given per os twice daily after oxygen exposure (from P15 to P21). Flash electroretinograms were recorded at P29 to assess the retinal function. At P31, retinas were extracted, sectioned and stained with toluidine blue to measure the thicknesses of the different retinal layers.

3.2 Results (Data Not Shown)

Hyperoxia caused a reduction in the scotopic and photopic b-wave amplitudes ($p<0.05$) and in thickness of the outer plexiform layer (OPL). Compared to the rat pups exposed to room air only; ROP rats treated with sildenafil showed an improvement in scotopic and photopic b-wave amplitudes ($p<0.05$). Sildenafil also improved OPL thickness in ROP animals ($p<0.05$).

Therefore, treatment with sildenafil following oxygen exposure provided a recovery of the function and structure of the retina.

While the disclosure has been described in connection with specific embodiments thereof, it will be understood that the scope of the claims should not be limited by the preferred embodiments set forth in the examples, but should be given the broadest interpretation consistent with the description as a whole.

ABBREVIATIONS cGMP, cyclic guanosine monophosphate; DAPI, 4,6-diamidino-2-phenylindole; ERG, electroretinogram; HI, hypoxia-ischemia; HIE, hypoxic-ischemic encephalopathy; INL, inner nuclear layer; IPL, inner plexiform layer; IS, inner segment; ONH, optic nerve head; ONL, outer nuclear layer; OPL, outer plexiform layer; OS, outer segment; P, postnatal; PDE5, phosphodiesterase type-5; PDE6, phosphodiesterase type-6; PhNR, photopic negative response; RGC/FL, retinal ganglion cell/fiber layer; RPE, retinal pigment epithelium; sild, sildenafil; veh, vehicle.

REFERENCES

Recker R, Adami A, Tone B, Tian H R, Lalas S, Hartman R E, Obenaus A, Ashwal S: Rodent neonatal bilateral carotid artery occlusion with hypoxia mimics human hypoxic-ischemic injury. J Cereb Blood Flow Metab 2009; 29: 1305-1316.

Hamers F P T, Koopmans G C, Joosten E: CatWalk-assisted gait analysis in the assessment of spinal cord injury. J Neurotrauma 2006; 23: 537-548.

Hetze S, Romer C, Teufelhart C, Meisel A, Engel O: Gait analysis as a method for assessing neurological outcome in a mouse model of stroke. J Neurosci Methods 2012; 206: 7-14.

Lubjuhn J, Gastens A, von Wilpert G, Bargiotas P, Herrmann O, Murikinati S, Rabie T, Marti H H, Amende I, Hampton T G, Schwaninger M: Functional testing in a mouse stroke model induced by occlusion of the distal middle cerebral artery. J Neurosci Methods 2009; 184: 95-103.

Parkkinen S, Ortega F J, Kuptsova K, Huttunen J, Tarkka I, Jolkkonen J: Gait impairment in a rat model of focal cerebral ischemia. Stroke Res Treat 2013; 2013: 410972.

Wang Y, Bontempi B, Hong S M, Mehta K, Weinstein P R, Abrams G M, Liu J: A comprehensive analysis of gait impairment after experimental stroke and the therapeutic effect of environmental enrichment in rats. J Cereb Blood Flow Metab 2008; 28: 1936-1950.

Rasband W S: ImageJ. Bethesda, Md.: U.S. National Institutes of Health, 1997-2004. Available at: http://imagej.nih.gov/ij/

Hendrickson M L, Rao A J, Demerdash O N, Kalil R E: Expression of nestin by neural cells in the adult rat and human brain. PLoS One 2011; 6: e18535.

Springer M L: Assessment of myocardial angiogenesis and vascularity in small animal models. Methods Mol Biol 2010; 660: 149-167.

Ndode-Ekane X E, Hayward N, Gröhn O, Pitkänen A: Vascular changes in epilepsy: functional consequences and association with network plasticity in pilocarpine-induced experimental epilepsy. Neuroscience 2010; 166: 312-332.

Hallene K L, Oby E, Lee B J, Santaguida S, Bassanini S, Cipolla M, Marchi N, Hossain M, Battaglia G, Janigro D: Prenatal exposure to thalidomide, altered vasculogenesis, and CNS malformations. Neuroscience 2006; 142: 267-283.

Iwai M, Cao G, Yin W, Stetler R A, Liu J, Chen J: Erythropoietin promotes neuronal replacement through revascularization and neurogenesis after neonatal hypoxia/ischemia in rats. Stroke 2007; 38: 2795-2803.

Noguchi T, Yoshiura T, Hiwatashi A, Togao O, Yamashita K, Nagao E, Shono T, Mizoguchi M, Nagata S, Sasaki T, Suzuki S O, Iwaki T, Kobayashi K, Mihara F, Honda H: Perfusion imaging of brain tumors using arterial spin-labeling: Correlation with histopathologic vascular density. Am J Neuroradiol 2008; 29: 688-693.

Rigau V, Morin M, Rousset M C, de Bock F, Lebrun A, Coubes P, Picot M C, Baldy-Moulinier M, Bockaert J, Crespel A, Lerner-Natoli M: Angiogenesis is associated with blood-brain barrier permeability in temporal lobe epilepsy. Brain 2007; 130: 1942-1956.

Wintermark P, Lechpammer M, Warfield S K, Kosaras B, Takeoka M, Poduri A, Madsen J R, Bergin A M, Whalen S, Jensen F E: Perfusion imaging of focal cortical dysplasia using arterial spin labeling: Correlation with histopathological vascular density. J Child Neurol 2013; 28: 1474-1482.

Shaikh H, Lechpammer M, Jensen F E, Warfield S K, Hansen A H, Kosaras B, Takeoka M, Poduri A, Madsen J R, Bergin A M, Whalen S, Jensen F E: Increased brain perfusion persists over the first month of life in term asphyxiated newborns treated with hypothermia: Does it reflect activated angiogenesis? Transl Stroke Res 2015; 6: 224-33.

Tong X K, Nicolakakis N, Kocharyan A, Hamel E: Vascular remodeling versus amyloid beta-induced oxidative stress in the cerebrovascular dysfunctions associated with Alzheimer's disease. J Neurosci 2005; 25: 11165-11174.

Foresta C, Caretta N, Zuccarello D, et al. Expression of the PDE5 enzyme on human retinal tissue: new aspects of PDE5 inhibitors ocular side effects. Eye (Lond). 2008; 22:144-149.

Hood D C, Birch D G. The A-wave of the human electroretinogram and rod receptor function. Invest Ophthalmol Vis Sci. 1990; 31:2070-2081.

Miller R F, Dowling J E. Intracellular responses of the Muller (glial) cells of mudpuppy retina: their relation to b-wave of the electroretinogram. J Neurophysiol. 1970; 33:323-341.

Stockton R A, Slaughter M M. B-wave of the electroretinogram. A reflection of ON bipolar cell activity. J Gen Physiol. 1989; 93:101-122.

Jung S, Polosa A, Lachapelle P, Wintermark P. Visual Impairments Following Term Neonatal Encephalopathy: Do Retinal Impairments Also Play a Role? Invest Ophthalmol Vis Sci. 2015; 56:5182-5193.

Li B, Barnes G E, Holt W F. The decline of the photopic negative response (PhNR) in the rat after optic nerve transection. Doc Ophthalmol. 2005; 111:23-31.

Machida S, Raz-Prag D, Fariss R N, Sieving P A, Bush R A. Photopic ERG negative response from amacrine cell signaling in RCS rat retinal degeneration. Invest Ophthalmol Vis Sci. 2008; 49:442-452.

What is claimed is:

1. A method for treating a brain and/or a retinal injury caused by an exposure to hyperoxia or hypoxia in a newborn having the brain and/or the retinal injury, the method comprising administering a first therapeutically effective dose of the phosphodiesterase inhibitor or a pharmaceutically acceptable salt at least 12 hours after the onset of the brain and/or the retinal injury so as to treat the brain and/or the retinal injury.

2. The method of claim 1, wherein the phosphodiesterase inhibitor is a selective phosphodiesterase inhibitor.

3. The method of claim 2, wherein the selective phosphodiesterase inhibitor is a phosphodiesterase type 5 selective inhibitor.

4. The method of claim 3, wherein the phosphodiesterase type 5 selective inhibitor is sildenafil.

5. The method of claim 4, wherein the pharmaceutically acceptable salt is a citrate salt.

6. The method of claim 1, wherein the phosphodiesterase inhibitor is administered orally.

7. The method of claim 6, wherein the phosphodiesterase inhibitor is administered twice daily.

8. The method of claim 6, wherein the phosphodiesterase inhibitor is administered at a dosage of from 2 mg/kg to 50 mg/kg.

9. The method of claim 1, wherein the phosphodiesterase inhibitor is administered during 7 consecutive days.

10. The method of claim 1, wherein the newborn is a premature baby.

11. The method of claim 1, wherein the newborn is a term baby.

12. The method of claim 1, wherein the newborn is a human baby.

13. The method of claim 1, for treating the brain injury.

14. The method of claim 1 for treating the retinal injury.

15. The method of claim 1, wherein the injury is caused by hyperoxia.

16. The method of claim 1, wherein the injury is caused by hypoxia.

17. The method of claim 1, wherein the phosphodiesterase inhibitor is administered orally.

* * * * *